(12) United States Patent
Schmidt

(10) Patent No.: US 12,220,599 B2
(45) Date of Patent: *Feb. 11, 2025

(54) WEARABLE PHOTOTHERAPY APPARATUS WITH ANTI-VIRAL AND OTHER EFFECTS

(71) Applicant: SOLETLUNA HOLDINGS, INC., San Diego, CA (US)

(72) Inventor: David Schmidt, San Diego, CA (US)

(73) Assignee: SOLETLUNA HOLDINGS, INC., San Diego, CA (US)

( * ) Notice: Subject to any disclaimer, the term of this patent is extended or adjusted under 35 U.S.C. 154(b) by 645 days.

This patent is subject to a terminal disclaimer.

(21) Appl. No.: 17/549,571

(22) Filed: Dec. 13, 2021

(65) Prior Publication Data

US 2022/0096861 A1 Mar. 31, 2022

Related U.S. Application Data

(63) Continuation-in-part of application No. PCT/US2020/035856, filed on Jun. 3, 2020, which is a continuation-in-part of application No. 16/438,364, filed on Jun. 11, 2019, now Pat. No. 10,716,953.

(51) Int. Cl.
 *A61N 5/06* (2006.01)
 *A61K 33/34* (2006.01)
 *A61K 41/00* (2020.01)

(52) U.S. Cl.
 CPC .............. *A61N 5/062* (2013.01); *A61K 33/34* (2013.01); *A61K 41/0057* (2013.01); *A61N 5/0624* (2013.01); *A61N 5/0616* (2013.01); *A61N 2005/0645* (2013.01); *A61N 2005/0659* (2013.01); *A61N 2005/0666* (2013.01)

(58) Field of Classification Search
 None
 See application file for complete search history.

(56) References Cited

U.S. PATENT DOCUMENTS

| | | | |
|---|---|---|---|
| 5,386,012 A | 1/1995 | Strid | |
| 6,974,799 B2 | 12/2005 | Lintner | |
| 8,653,925 B2 | 2/2014 | Schmidt | |
| 8,734,316 B2 | 5/2014 | Schmidt | |
| 8,743,316 B2 * | 6/2014 | Jung | G02B 6/0088 349/63 |
| 9,314,417 B2 | 4/2016 | Perricone | |
| 9,943,672 B2 * | 4/2018 | Schmidt | A61K 9/7023 |
| 10,716,953 B1 * | 7/2020 | Schmidt | A61K 31/198 |
| 10,898,724 B2 * | 1/2021 | Schmidt | A61K 31/315 |
| 2004/0057983 A1 | 3/2004 | Schmidt | |
| 2007/0148222 A1 | 6/2007 | Dorogi et al. | |
| 2011/0106227 A1 | 5/2011 | Desiderio et al. | |
| 2011/0184356 A1 | 7/2011 | Schmidt | |
| 2014/0188025 A1 | 7/2014 | Aziz | |
| 2016/0166502 A1 | 6/2016 | Schmidt | |
| 2017/0224760 A1 | 8/2017 | Garruto et al. | |
| 2018/0055933 A1 | 3/2018 | Vissman et al. | |
| 2018/0071547 A1 | 3/2018 | Decaux et al. | |

FOREIGN PATENT DOCUMENTS

| | | |
|---|---|---|
| EP | 0522004 A | 1/1993 |
| EP | 3750594 A1 | 12/2020 |
| WO | 9114437 | 10/1991 |
| WO | 2020251816 A1 | 12/2020 |

OTHER PUBLICATIONS

Office Action issued in KR10-2021-7025322 on Dec. 22, 2021, and English translation thereof.
Final Office Action issued in KR10-2021-7025322 on Jul. 18, 2022, and English translation thereof.
Notification of Granted Patent issued in IDP00202104146 on Aug. 11, 2023, and translation thereof.
Examiner Requisition issued in CA3,125,207 on Sep. 28, 2023.
Application Found Allowable notice issued in CA3,125,207 on Dec. 8, 2023.
Modified Substantive Examination Examiner's Report received in Application PI2021002455 on May 30, 2023.
Canadian Examination Report Received in CA3,125,207 on Mar. 22, 2023 (5 pages).
Extended European Search Report issued in 22172030.3 on Sep. 27, 2022 (17 pages).
European Search Report received in EP20177970.9-1122, dated Jul. 24, 2020 (14 pages).
Loren Pickart, et al, "Regenerative and Protective Actions of the GHK-CU Peptide in the Light of the New Gene Data", International Journal of Molecular Sciences; vol. 19, No. 7, Jul. 7, 2018 (13 pages).
Connor, et al., "Metabolic Implications of the Lifewave X39 Patch", 2019, 59 pages.
"Experimental Study of Lifewave, Inc. X-39 Patches", The Centre for Biofield Sciences Integrated Health, Nov. 23, 2018, 28 pages.
Nutrinoche News (Top 10 Benefits & Uses of Colloidal Copper), Oct. 9, 2017.
PubChem, accessed Aug. 14, 2019.
Creative Peptides (What is GHK and Copper Peptide? Apr. 17, 2017).

(Continued)

*Primary Examiner* — Melissa S Mercier
(74) *Attorney, Agent, or Firm* — ARC IP Law, PC; Joseph J. Mayo

(57) ABSTRACT

Embodiments enables a wearable phototherapy apparatus that produces beneficial effects to a human body such as anti-viral effects, activation of stem cells, improvement in strength, improvement in stamina, pain relief via a non-transdermal container. May include an optional transdermal container that releases or increases copper peptide GHK-Cu in a subject's body. The non-transdermal apparatus reflects or emits specific wavelengths of light to elevate levels of the copper peptide GHK-Cu in the body. The non-transdermal apparatus includes one or more materials that prevent the Left-Handed molecule from direct contact with the body while the enclosure is coupled to the body and prevents the Left-Handed molecules from entering the body. Embodiments may include or be used with any bioavailable form of copper, e.g., such as copper glycinate as an anti-viral therapy and may include an anti-inflammatory or both.

17 Claims, 12 Drawing Sheets

(56) References Cited

OTHER PUBLICATIONS

International Search Report and Written Opinion issued in PCT/US20/35856; mailed Sep. 18, 2020 (8 pages).
Wang, et al., "Hyaluronic Acid Encapsulated CuS Gel-Mediated Near-Infrared Laser-Induced Controllable Transdermal Drug Delivery for Sustained Therapy" ACS Sustainable Chem. Eng. 2017, vol. 5. No. 8; pp. 6786-6794; abstract, para 6788, col. 2, para 1.
International Preliminary Report on Patentability issued in PCT/US20/35856; mailed Jun. 30, 2020 (7 pages).

* cited by examiner

WEARABLE PHOTOTHERAPY APPARATUS WITH ANTI-VIRAL AND OTHER EFFECTS

This application is a continuation-in-part of Patent Cooperation Treaty Patent Application PCT/US20/35856, filed 3 Jun. 2020, which is a continuation-in-part of U.S. Utility patent application Ser. No. 16/438,364, filed 11 Jun. 2019, the specification of which is hereby incorporated herein by reference.

BACKGROUND OF THE INVENTION

Field of the Invention

Embodiments of the invention generally relate to a wearable phototherapy apparatus that includes a non-transdermal container with Left-Handed molecules wherein the container reflects or emits specific wavelengths of light to stimulate nerves and in some embodiments, also acupuncture points. More particularly, but not by way of limitation, in one or more embodiments, the wearable phototherapy apparatus elevates specific peptides in a user including GHK, which is also known as tripeptide-1 and/or GHK-Cu, which is also known as copper peptide. More particularly, but not by way of limitation, in one or more embodiments, the wearable phototherapy apparatus produces beneficial effects in human beings and animals, in some embodiments as a result of elevating copper peptide, including anti-viral effects, activation of stem cells, improvements in energy, elevation of antioxidants, reduction in inflammation, management of pain, improvements in stamina, elevation of collagen production, improved wound healing and other beneficial health effects, e.g., in some cases as attributed to copper peptide as well as benefits associated with stimulating the nerves and in some embodiments, also acupuncture points with light. Embodiments may include, or be used with any form of bioavailable copper, for example copper glycinate as an anti-viral therapy and embodiments may include, or be used with an anti-inflammatory or both bioavailable copper and an anti-inflammatory. At least one embodiment may be utilized to treat the novel coronavirus (COVID-19) through light mediated synthesis of copper peptide and mobilization of copper ions for example.

Description of the Related Art

Jewelries including ring, necklace, bracelets, and pendants are typically used for decorative purpose. However, there is a segment of the jewelry market that concerns itself for a purpose other than decorative. Examples of jewelries that are designed for the purpose other than decorative include copper bracelets and magnetic jewelries.

Copper bracelets are believed to perform functions of relieving pain and helping to alleviate symptoms of arthritis for a user. A mode of operation for these functions has been proposed as mobility of copper ions from the copper bracelet through the user's skin and into the user's blood stream. If the mobility of copper ions is the mode of operation of a copper bracelet, then an individual or a user could not obtain immediate relief from pain, etc., due to a long period of time required for this mode of operation to become effective. Accordingly, a drawback of existing systems with respect to a copper bracelet is that the therapeutic response, if any, takes place over a relatively long period of time. Another drawback of the existing systems is that the copper bracelets have a limited and narrow field of use.

Various types of magnetic jewelries are believed to perform functions of relieving pain and improving circulation. Clinical studies performed with magnetic jewelries indicated that there is an effect going on other than a placebo effect. An effect of a magnet on a human body could be due, in part, to the fact that human blood contains iron. In one theory, the iron in the blood causes the blood to be attracted to a part of the body in which the magnet is worn, resulting in improvement in circulation. However, there are biophysicists who question the efficacy of a magnetic jewelry. For example, it is well known that the DNA contains Hydrogen bonds. Because a magnet is polar in nature, a back EMF from the magnet to the Hydrogen bonds may be possible. This might cause the hydrogen to spin in opposition to what is normal and disassemble the DNA of that cell. In any case, long term studies of magnets as they apply to humans are needed. Another drawback of the existing systems with respect to a magnetic jewelry, is that the therapeutic response, if any, is limited and narrow with respect to the field of use.

Therefore, with respect to jewelries that may be utilized for the purpose of achieving a therapeutic effect, there is a need for an alternative to the copper bracelet and the magnetic jewelries that are found in the present market. Such alternative may require a mode of operation that is different from the modes of operation of the existing copper bracelet and magnetic jewelries. In this regard, an examination of alternative modes of operation for a passive therapeutic jewelry needs to be considered.

In addition, the body of evidence supporting acupuncture has reached the point of being irrefutable. This said, a conclusion may be reached that in addition to blood flowing through the human body, there is also an energy flow through the human body.

As an example, in acupuncture, a practitioner utilizes known techniques to detect "blockages" to energy flows in the human body. When the locations of these blockages are determined, then either needles or pressure is applied to this point for the purpose of relieving and removing the blockages. Accordingly, another drawback of the existing systems is a lack of an apparatus that can be placed over specific acupuncture points and that can interact with a humans' energy field and promote energy flow and circulation in a similar mode of operation to acupuncture but without needles or physical contact.

Various chemical species in the human body and biochemical materials may also need to be considered since they may play a role in interacting with energy fields within the human body. To this end, Left-Handed molecules may need to be considered. Generally, the Left-Handed group of molecules known as amino acids are utilized in the body for the purpose of building protein structures. This process of the amino acid forming a "building block" for a larger protein structure is generally recognized as being a solely chemical process, and existing systems lack any other processes that create a buildup of energy to assist in forming a new protein structure.

Therefore, another drawback of the existing system is a lack of an apparatus and a method for regulating the energy-flow, thereby producing a beneficial response within the human body.

Phototherapy devices currently on the market include things such as lasers, lamps and LED products. These products are typically designed to produce very specific wavelengths of light. For example, there are phototherapy devices which produce 660 nm light for stimulating energy production in the body and increasing collagen production or stimulating hair growth. In addition, these devices require a power source and are not disposable.

Generally, there are patches on the market, and most of these are transdermal devices that deliver drugs or herbs through the skin.

These and other drawbacks also exist in the known art and for these reasons there is a need for a wearable phototherapy apparatus, for example that does not require a power source and can be constructed to be a disposable device, that solves these problems and that produces the benefits as stated herein.

BRIEF SUMMARY OF THE INVENTION

Embodiments of the invention overcome the problems previously described above. In one or more embodiments, the novel apparatus described herein is designed to reflect or emit specific wavelengths of light that will trigger the production of copper peptide or elevate other peptides to produce the benefits associated with the phototherapy devices of the invention presented herein. In biology this is known as photobiomodulation. A good example is how UV light will cause the product of Vitamin D. This is an example of how light causes changes in the biochemistry of the body. In one or more embodiments of the invention, the apparatus, such as a non-transdermal patch, may produce benefits including increasing the metabolism of one or more different amino acids and elevating neurotransmitters. In at least one embodiment requires no source of power, unlike conventional phototherapy devices and may be applied anywhere to the body where treatment is desired. Embodiments may be configured as a disposable device, making it cost effective compared to other phototherapy devices and may be configured as a non-transdermal patch, wherein no chemicals are based into the body. In one or more embodiments, stimulation of the skin occurs with light.

Embodiments may include, or be used with, copper glycinate as an anti-viral therapy or an anti-inflammatory or both. At least one embodiment may be utilized to treat the novel coronavirus (COVID-19) through light mediated synthesis of copper peptide and mobilization of copper ions for example. Benefits of this therapy include:

Produces rapid alterations in blood chemistry for powerful antiviral effects
Large body of evidence to support efficacy
Simple to administer
Reduced risk of toxic side effects
Inexpensive
Large scale manufacturing already in place for immediate deployment Embodiments of the invention target viruses through administration of any form of bioavailable copper, in one embodiment administered orally, in other embodiments via transdermal patches, or via injection, combined with embodiments described herein that are configured to light mediate the synthesis of peptide GHK that binds to copper for producing powerful antiviral effects. Embodiments may be utilized with anti-inflammatory drugs, e.g., either taken orally or administered via transdermal patches or induced by non-transdermal patches for example.

In one embodiment, the invention provides an apparatus or system that produces a beneficial effect when placed on a human body. For example, the beneficial effect may include, increasing the metabolism of one or more amino acids, elevating neurotransmitters, elevation of GHK and/or GHK-Cu, activation of stem cells, improvements in a user's energy, strength increase, stamina increase, pain relief, improved wound healing and other health benefits. In at least one embodiment of the invention, to produce a beneficial effect when placed on a human body, a change in the biochemistry of the body may be produced via one or more of proteinogenic amino acids, non-proteinogenic amino acids, L-amino acid, non-standard amino acids, human nutrition and non-protein functions.

In one embodiment, the invention provides an apparatus that produces a beneficial effect when placed on a human body, wherein the apparatus, such as a phototherapy device, provides phototherapy within the human body for producing the beneficial effect, for example via a non-transdermal patch.

In one embodiment, the invention provides an apparatus, such as the phototherapy device, that includes biomolecular components and one or more substrates, for example, but not limited to a polyester, cotton labor sheet, etc., for the biomolecular components that reflect or emit wavelengths of light for the phototherapy device.

In one embodiment, the invention provides an apparatus including biomolecular components associated with reflection of specific wavelengths of light, wherein the biomolecular components may include, for example, but not limited to a Left-Handed molecule such as an amino acid (e.g., L-Glutamine).

In at least one embodiment of the invention, the system includes a first layer that may include a transdermal patch and a second layer that may include a non-transdermal patch. In one or more embodiments, the first layer consists essentially of copper peptide GHK-Cu and other materials that are known in the art of transdermal patches such as adhesive, such that the first layer may deliver the copper peptide GHK-Cu into the subject's body. In at least one embodiment of the invention, the system includes a second layer coupled to the first layer, wherein the second layer includes a non-transdermal container having at least one Left-Handed material and/or materials capable of reflecting or emitting wavelengths of light capable of activating receptors in the body that increase production of GHK and/or GHK-Cu, water, and any necessary preservatives such as glycerol. In one or more embodiments, the second layer may include a plurality of Left-Handed material containers simultaneously applied to the subject's body.

By way of at least one embodiment, the second layer is coupled on top of the first layer, i.e., away from the skin of the user.

In one or more embodiments of the invention, the first layer is directly coupled to the second layer side by side. In at least one embodiment, the first layer is indirectly coupled to the second layer, such that the first layer attaches to a first portion of the subject's body and the second layer attaches to a second portion of the subject's body.

According to at least one embodiment of the invention, the first layer may deliver chemicals and nutrients to the subject's body, and the second layer does not deliver such chemicals and nutrients to the subject's body, for example when applied simultaneously.

In one embodiment, the invention provides an apparatus including one or more substrates, for example, but not limited to a polyester, cotton labor sheet, etc., for biomolecular components that reflect or emit wavelengths of light for the phototherapy device.

In one embodiment, the invention provides an apparatus including a sealed plastic enclosure, wherein the sealed plastic enclosure may enclose biomolecular components that reflect or emit wavelengths of light for the phototherapy device.

In one embodiment, the invention provides an apparatus that includes a sealed plastic enclosure having biomolecular components that reflect or emit wavelengths of light for the phototherapy device, wherein the apparatus may further include water and preservatives.

In one embodiment, the invention provides one or more physical structural settings for holding components of an apparatus. In some embodiments, said one or more physical structural settings may hold biomolecular components that reflect or emit wavelengths of light for the phototherapy device, one or more substrates for said biomolecular components, water and preservatives.

In one embodiment, the invention provides an apparatus that produces a beneficial effect, for example elevation of GHK and/or GHK-Cu for activation of stem cells, when placed on a human body, wherein the apparatus may comprise one or more of components including, for example, Left-Handed molecules (e.g., L-Glutamine), one or more materials that reflect or emit wavelengths of light capable of elevating GHK and/or GHK-Cu, one or more substrates (e.g., a polyester, cotton fabric sheet, etc.) for said Left-Handed molecules, a sealed enclosure (e.g., plastic film enclosure) enclosing said Left-Handed molecules and said one or more substrates, water and preservatives. One or more embodiments are packaged as non-transdermal patches for example.

By way of one or more embodiments, Left-Handed group of molecules, such as amino acids, may be utilized in the body to build protein structures such as muscle tissue. At least one embodiment of the invention includes a Left-Handed (such as amino acids that are isomers and present optical chirality) material-containing apparatus, for example an L-amino acid, wherein light passing through an amino acid will bend to the left, and one or more materials that reflect or emit wavelengths of light capable of elevating GHK and/or GHK-Cu. Accordingly, in one or more embodiments, at the molecular level, in the process of the amino acid being used to form a protein, one or more materials that reflect or emit wavelengths of light capable of elevating GHK and/or GHK-Cu, or other peptides and biochemical that produce the benefits discussed herein.

By way of at least one embodiment, the left-handed material-containing apparatus includes materials specifically pre-selected because such materials may interact with the infrared heat (light) being emitted by the human body, and thus stimulate the materials inside the patch causing them to reflect specific wavelengths of light back to the body (phototherapy). In one or more embodiments, a packet of photons, such as one packet or small amounts of light, may stimulate a human receptor to activate the receptor, such that only very small amounts of energy are required to cause the photobiomodulation effect.

By way of one or more embodiments, the non-transdermal patch may include two phototherapy layers as a first phototherapy layer and a second phototherapy layer. In at least one embodiment, the first phototherapy layer and the second phototherapy layer are layered and coupled on top of each other, such that one layer of the two phototherapy layers is layered and coupled on top of a second layer of the two phototherapy layers. In one or more embodiments, the first phototherapy layer and the second phototherapy layer are layered and coupled as concentric rings. In one or more embodiments, for example, the first phototherapy layer and the second phototherapy layer may be placed next to one another and coupled directly or indirectly. In at least one embodiment, via the two phototherapy layers, the non-transdermal patch reflects different wavelengths of light from each layer of the first phototherapy layer and the second phototherapy layer, therefore producing additional beneficial biological effects.

According to one or more embodiments, the phototherapy apparatus may deliver ingredients to the subject's body that complement the function of GHK-Cu, via one or more patches or layers. In at least one embodiment, the ingredients may include minerals such as copper, zinc, selenium, magnesium and sulphur, wherein such ingredients support wound healing and thus provide an advantage to the subject's body.

In one embodiment, the invention provides an apparatus that may be in one or more of a plurality of wearable objects such as, but not limited to, dermal patches, bracelets, pendants, support pads, shirts, socks, foot inserts, etc.

In some embodiments, the invention provides a non-transdermal patch having Left-Handed molecules for improving strength/stamina for a user.

In one embodiment, the invention provides a method for placing an apparatus on a human body or into a human body, wherein the apparatus produces a beneficial effect when placed on the human body or into the human body, wherein the apparatus includes biomolecular components associated with reflection of specific wavelengths of light, wherein the biomolecular components may include, for example, but not be limited to a Left-Handed molecule such as an amino acid (e.g., L-Carnitine).

In at least one embodiment of the invention, the method includes applying the first layer to the subject's body and applying the second layer to the subject's body.

By way of one or more embodiments, the non-transdermal patch may include at least one ball or bead. In at least one embodiment, the at least one ball or bead may be or may include plastic. In one or more embodiments, the at least one ball or bead may be located at the bottom of the non-transdermal patch, such as underneath the non-transdermal patch at an outer surface of the non-transdermal patch. In at least one embodiment, the at least one ball or bead may be located underneath the non-transdermal patch, wherein the at least one ball or bead directly or indirectly contacts the user's skin. In one or more embodiments, the at least one ball or bead may be located between layers of the non-transdermal patch, such as for example between the first layer and the second layer of the non-transdermal patch. By way of at least one embodiment, the at least one ball or bead may stimulate the user's skin with mild pressure. According to one or more embodiments of the invention, the at least one ball or bead may stimulate specific points on the user's skin to provide additional beneficial biological effects, such as to mobilize stem cells of the user.

Other objects and features will become apparent from the following detailed description considered in connection with the accompanying drawings that disclose embodiments of the invention. It should be understood, however, that the drawings are designed for purposes of illustration only and not as a definition of the limits of the invention.

BRIEF DESCRIPTION OF THE DRAWINGS

The above and other aspects, features and advantages of at least one embodiment of the invention will be more apparent from the following more particular description thereof, presented in conjunction with the following drawings, wherein.

2A illustrates an example of an apparatus including a single layer fabric substrate for retaining biomolecular components, according to an embodiment of the invention.

Figure 2A:
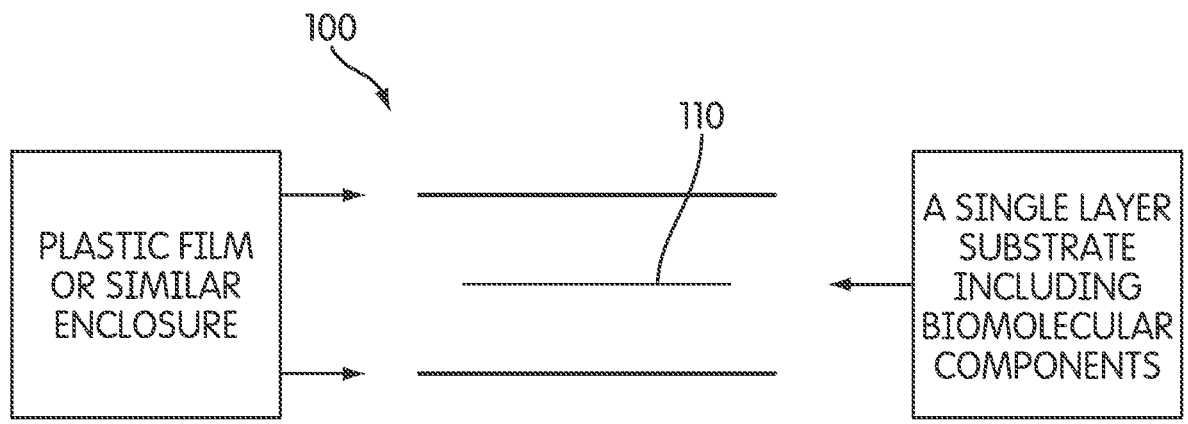
Figure 2B:
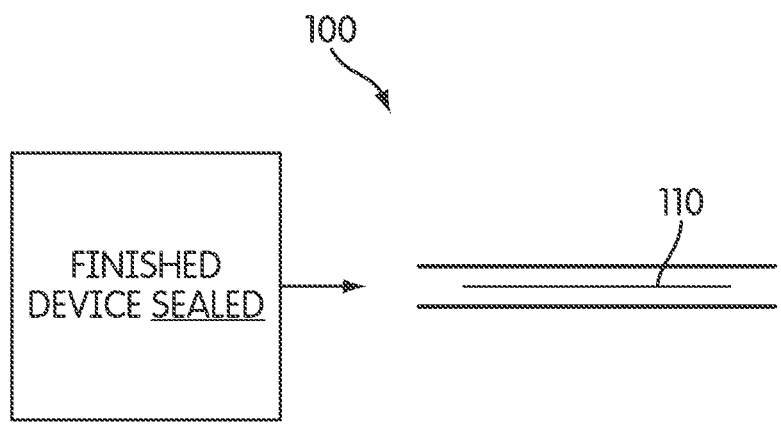

FIG. 2B illustrates an example of a sealed apparatus including a single layer fabric substrate for retaining biomolecular components, according to an embodiment of the invention.

Figure 3A:
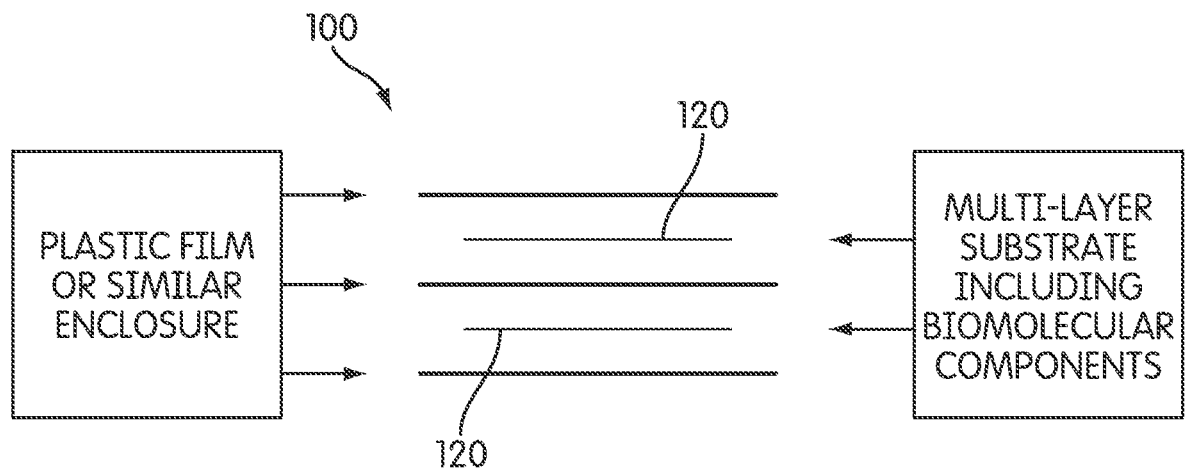

FIG. 3A illustrates an example of an apparatus including a multi-layer fabric substrate for retaining biomolecular components, according to an embodiment of the invention.

Figure 3B:
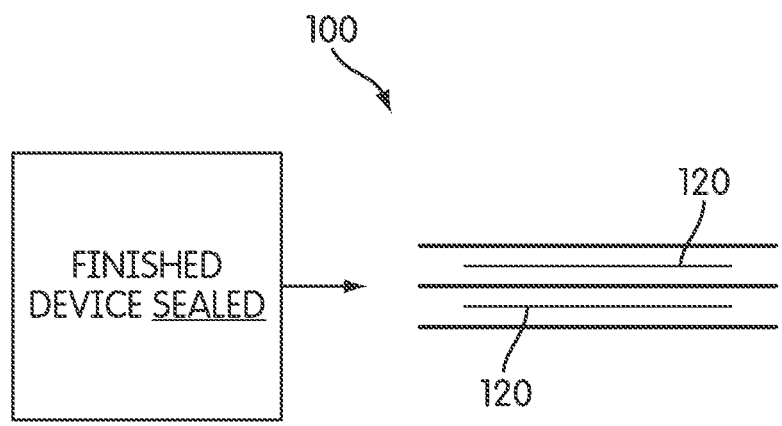

FIG. 3B illustrates an example of a sealed apparatus including a multi-layer fabric substrate for retaining biomolecular components, according to an embodiment of the invention.

Figure 4:
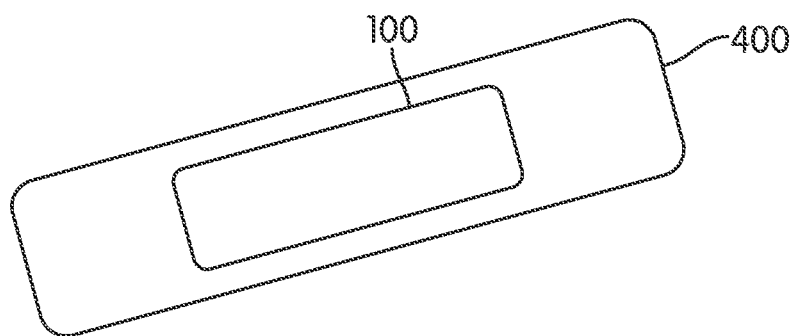

FIG. 4 illustrates an example of a patch including a biomolecular apparatus that causes a beneficial effect within a human body, according to an embodiment of the invention, and that may contain a non-transdermal apparatus.

Figure 5:
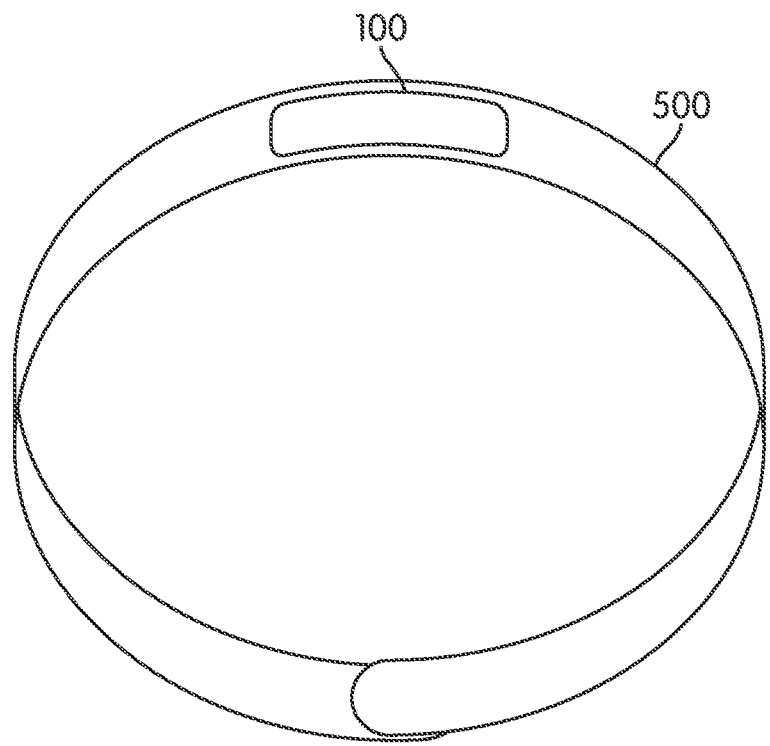

FIG. 5 illustrates an example of a bracelet including a biomolecular apparatus that causes a beneficial effect within a human body, according to an embodiment of the invention, and that may contain a non-transdermal apparatus.

Figure 6:
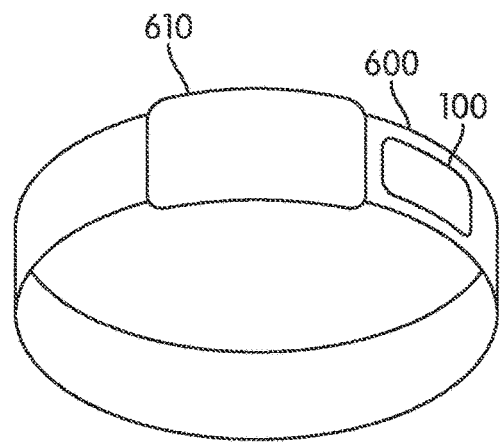

FIG. 6 illustrates an example of a ring including a biomolecular apparatus that causes a beneficial effect within a human body, according to an embodiment of the invention, and that may contain a non-transdermal apparatus.

Figure 7:
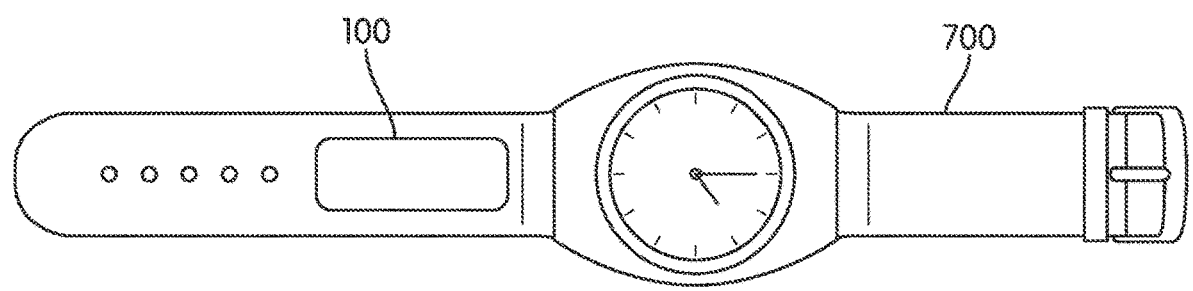

FIG. 7 illustrates an example of a watch including a biomolecular apparatus that causes a beneficial effect within a human body, according to an embodiment of the invention, and that may contain a non-transdermal apparatus.

Figure 8A:
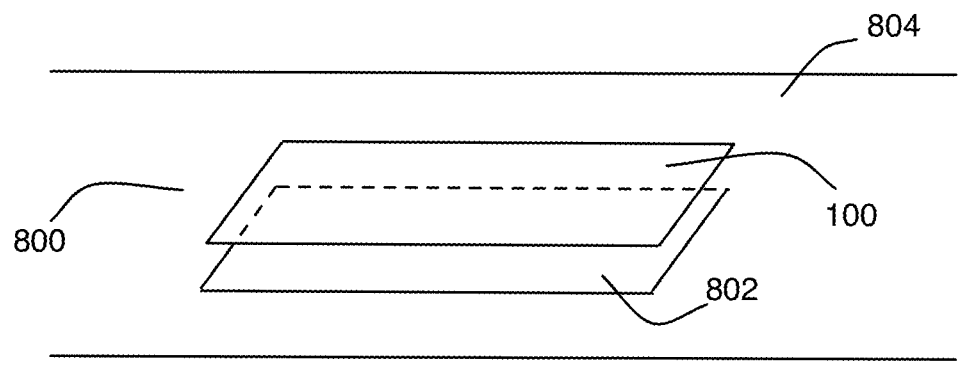

FIG. 8A illustrates a system that includes a first layer, and a second layer with a material-containing apparatus coupled on top of the first layer, according to one or more embodiments of the invention.

Figure 8B:
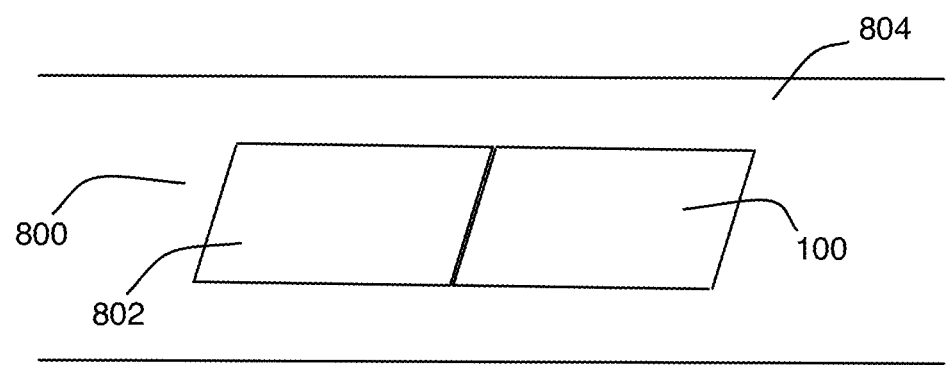

FIG. 8B illustrates a system that includes a first layer, and a second layer with a material-containing apparatus directly coupled to the first layer side by side, according to one or more embodiments of the invention.

Figure 8C:
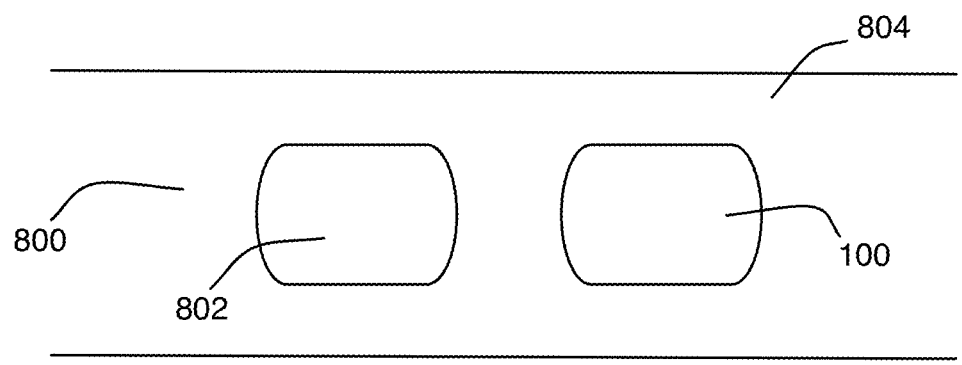

FIG. 8C illustrates a system that includes a first layer, and a second layer with a material-containing apparatus indirectly coupled to the first layer side by side, according to one or more embodiments of the invention.

Figure 8D:
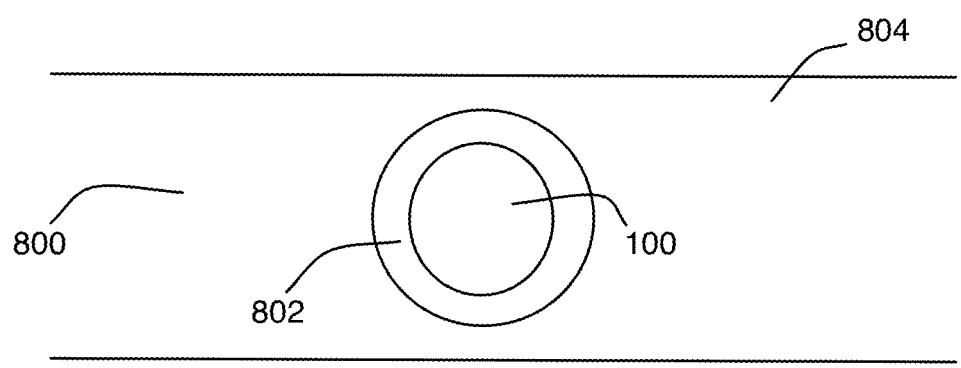

FIG. 8D illustrates a system that includes a first layer, and a second layer with a material-containing apparatus layered as concentric rings, according to one or more embodiments of the invention.

Figure 9A:
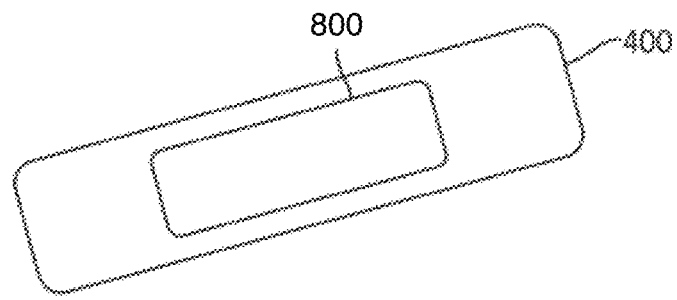

FIG. 9A illustrates an example of a patch including a system that causes a beneficial effect within a human body, according to an embodiment of the invention that contain at least one material that produces a photobiomodulation effect, and that may contain at least a non-transdermal apparatus and transdermal apparatus.

Figure 9B:
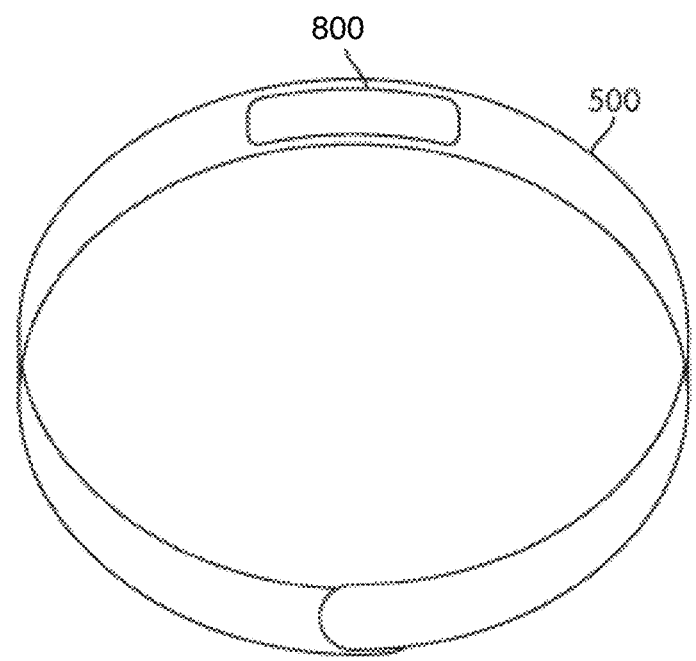

FIG. 9B illustrates an example of a bracelet including a system that causes a beneficial effect within a human body, according to an embodiment of the invention, and that may contain at least a non-transdermal apparatus and transdermal apparatus.

Figure 9C:
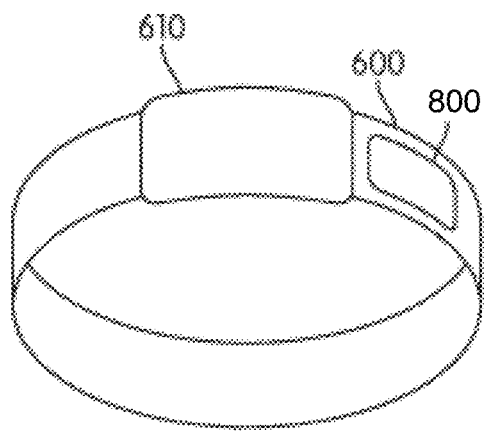

FIG. 9C illustrates an example of a ring including a system that causes a beneficial effect within a human body, according to an embodiment of the invention, and that may contain at least a non-transdermal apparatus and transdermal apparatus.

Figure 9D:
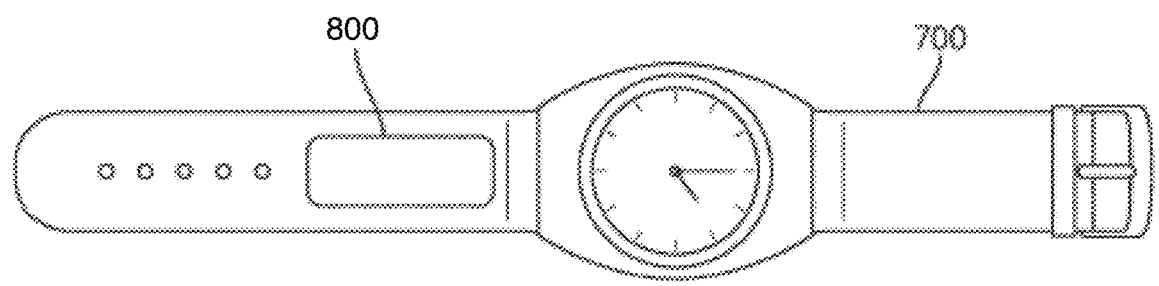

FIG. 9D illustrates an example of a watch including a system that causes a beneficial effect within a human body, according to an embodiment of the invention, and that may contain at least a non-transdermal apparatus and transdermal apparatus.

Figure 10A:
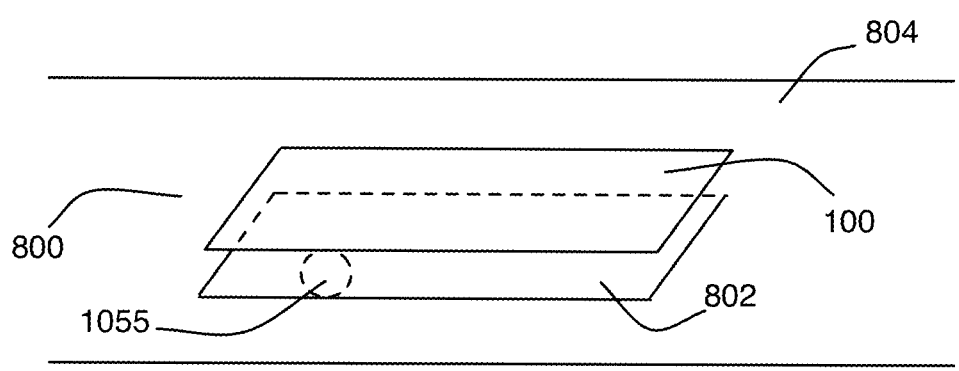

FIG. 10A illustrates a patch with at least one ball or bead located underneath the patch at an outer surface of the patch, according to one or more embodiments of the invention.

Figure 10B:
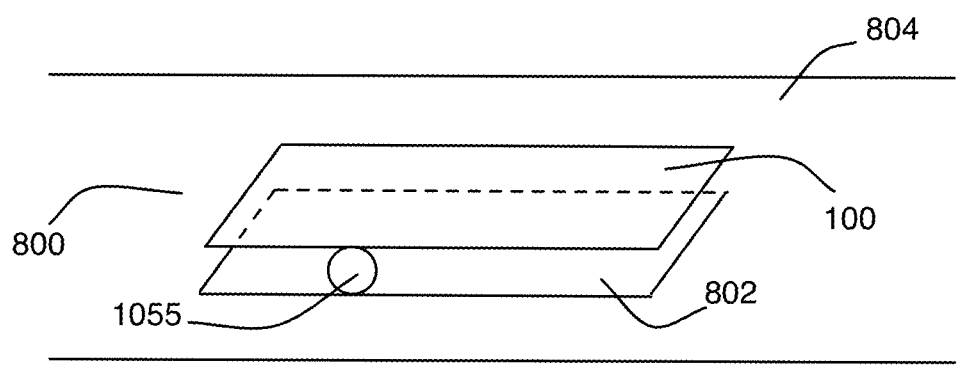

FIG. 10B illustrates a patch with at least one ball or bead located between layers of the patch, according to one or more embodiments of the invention.

Figure 11:
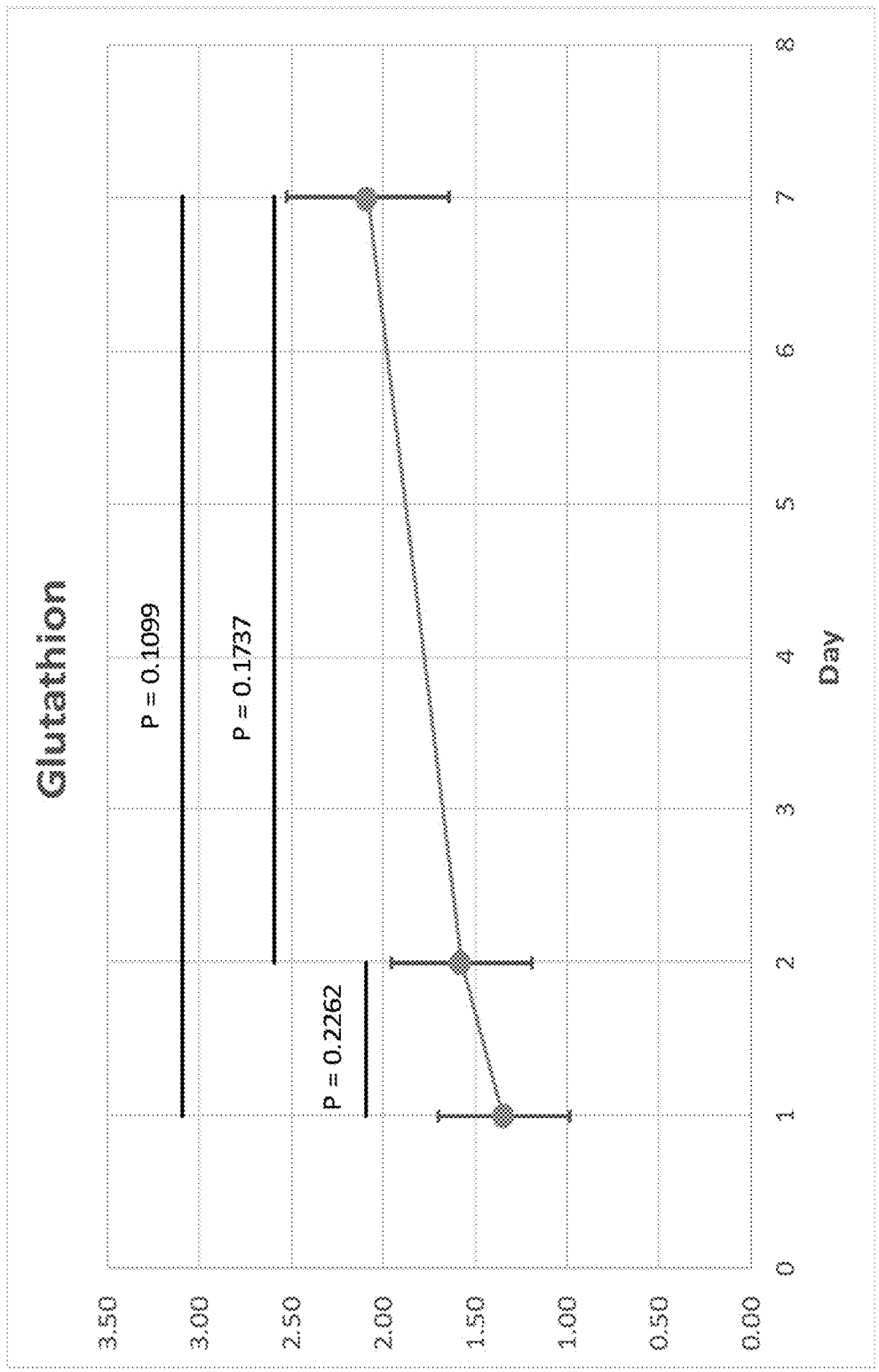

FIG. 11 illustrates an increase in production of Glutathione that supports the reduction of inflammation pathways that enables detoxification of the blood to act as an indirect anti-inflammatory agent.

Figure 12:
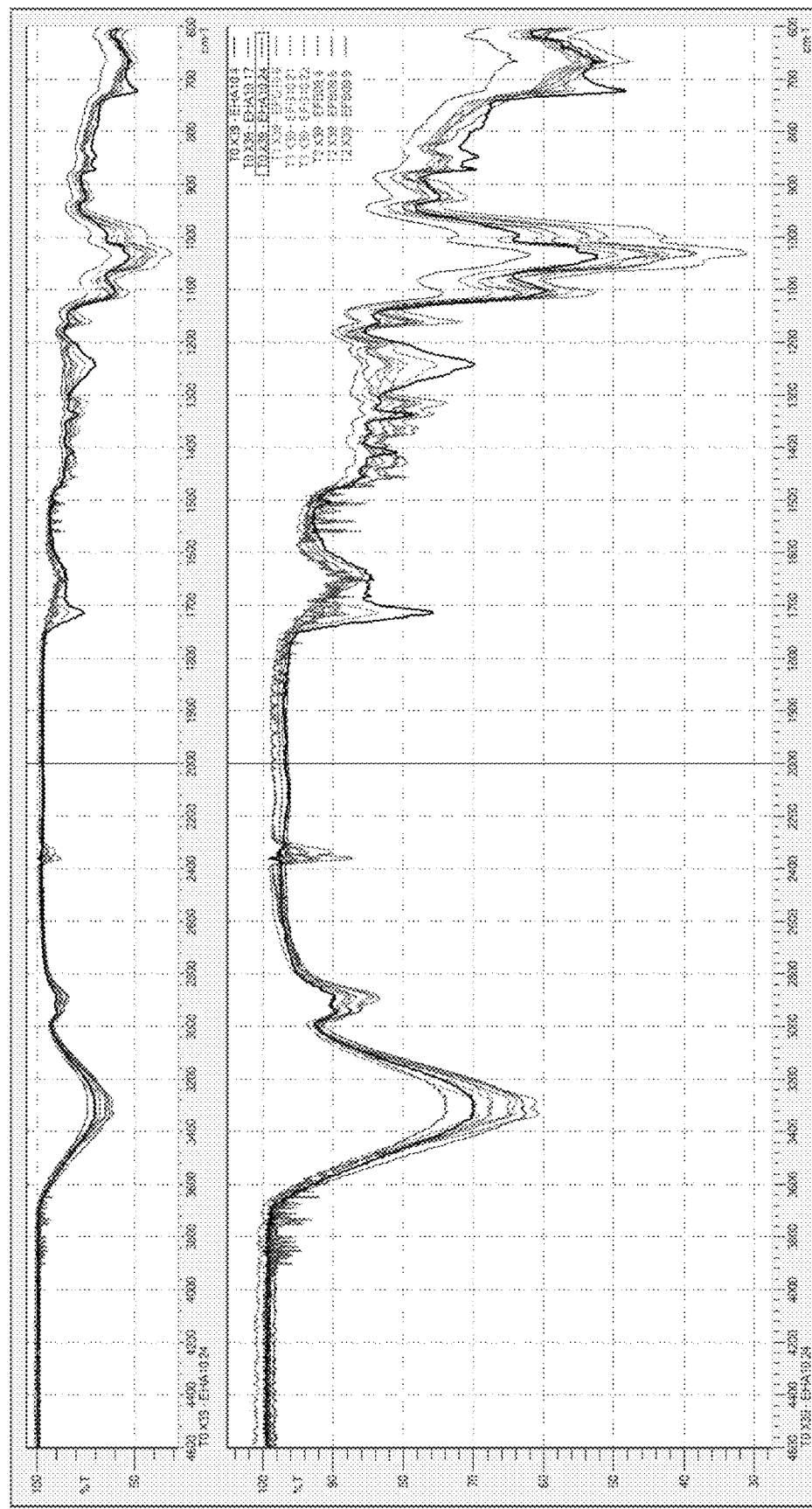

FIG. 12 shows results in the form of a Visual Comparison of a sample of patch spectra at T0 (Black), T1 (Blue), and T2 (Red).

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

According to at least one embodiment, the invention provides an apparatus that produces a beneficial effect when placed on a human body, wherein the apparatus at least provides phototherapy to the human body for producing the beneficial effect. In one or more embodiments, the beneficial effect may include, for example, strength increase, stamina increase, and pain relief. At least one embodiment of the invention provides an apparatus that includes a sealed plastic enclosure having biomolecular components that reflect or emit wavelengths of light for the phototherapy device, wherein the apparatus may further include water and preservatives.

According to at least one embodiment, the invention provides an apparatus that may include orthomolecular organic compounds (e.g., naturally occurring organic compounds) and or non-orthomolecular organic compounds for inducing one or more beneficial effects such as, for example, strength increase, stamina increase, pain relief, etc.

In at least one embodiment, in humans, an increase in electron flow has numerous demonstrable benefits with one being an immediate and measurable increase in physical strength. By way of one or more embodiments, this is not a chemically induced increase in strength such as would be the case with anabolic steroids, etc., but rather a phenomenon in which existing muscle mass is utilized more efficiently due to the increase in electron flow.

For example, by way of one or more embodiments, when examining the striated skeletal muscle apparatus, we know that this voluntary group nerve supply is under conscious control because these nerves are branches of the peripheral cerebrospinal nervous apparatus (the brain and spinal cord as the cerebrospinal axis). In at least one embodiment, the muscle fibers themselves are tissues composed of contractile cells that effect movement based on the excitatory process set up in nerve fibers by stimuli (the nerve impulse). It is presently believed by medical research that the nerve impulse is probably in the nature of a wave of electrochemical disturbances. In at least one embodiment, the efficiency with which the nerve impulse controls a specific muscle group can be defined as the number of muscle fibers utilized in a contraction divided by the number of fibers present in that muscle group. It is presently believed, according to one or more embodiments of the invention, that most humans only contract a small percentage of muscle fibers in a given group for a given nerve impulse (low efficiency of muscle mass usage per nerve impulse contraction).

According to one or more embodiments, when inducing a condition in which the total power of the electrochemical nerve impulse could be increased such that more muscle fibers could contract for a given nerve impulse, the net efficiency of the striated fibers would increase (more muscle fibers in a group being contracted for a nerve impulse), and hence usable physical strength could be improved. As such, by way of one or more embodiments, the beneficial effects are present, for example, immediate and demonstrable increases in strength and stamina within seconds of wearing the wearable apparatus according to one or more embodiments of the invention.

For example, by way of at least one embodiment, in physical therapy electrical signals are utilized for the purpose of forcing voluntary muscle groups to contract under stimulation. These devices are commonly known as electrical or electronic muscle stimulators (EMS) and cause stimulated contraction and relaxation phases of muscle groups. According to at least one embodiment, the invention provides an apparatus for, based on the mode of operation as presented, an improvement in net efficiency of total muscle mass utilized during a contraction phase that may be achieved due to an increase in electron flow during the wave of electrochemical disturbances created by the nerve impulse.

To understand this occurrence, the metabolic process involving fatty acid energy sources within the human body can be examined. In at least one embodiment, fatty acids, a hydrocarbon in which one of the hydrogen atoms has been replaced by a carboxyl group, are also described as a monobasic aliphatic acid made up of an alkyl radical attached to a carboxyl group. The metabolic role of fatty acids may be described in part in that fatty acids are one of the primary sources of energy for humans and, through Beta-Oxidation, are broken down into basic units of energy. Of interest here is that, in one or more embodiments, in order for this process to work, fatty acids need to enter the mitochondria for Beta-Oxidation, and they are unable to penetrate the inner mitochondrial membrane by themselves. In the human body, in at least one embodiment, to overcome the problem of the inability of fatty acids to transport from the cytosol (soluble portion of the cell) across the mitochondrial membrane, it has been determined by several researchers that various nutrients are essential to transport long chain fatty acids from the cytosol across the mitochondrial membrane for fatty acid oxidation/metabolism and energy production.

According to one or more embodiments of the invention, in order to obtain the desirable effect of improving cell metabolism passively (specifically, increasing the rate of fatty acid Beta-Oxidation by allowing fatty acids to transport across the mitochondrial membrane), an apparatus includes orthomolecular organic structures can be designed to passively interact with the human body.

Figure 1:
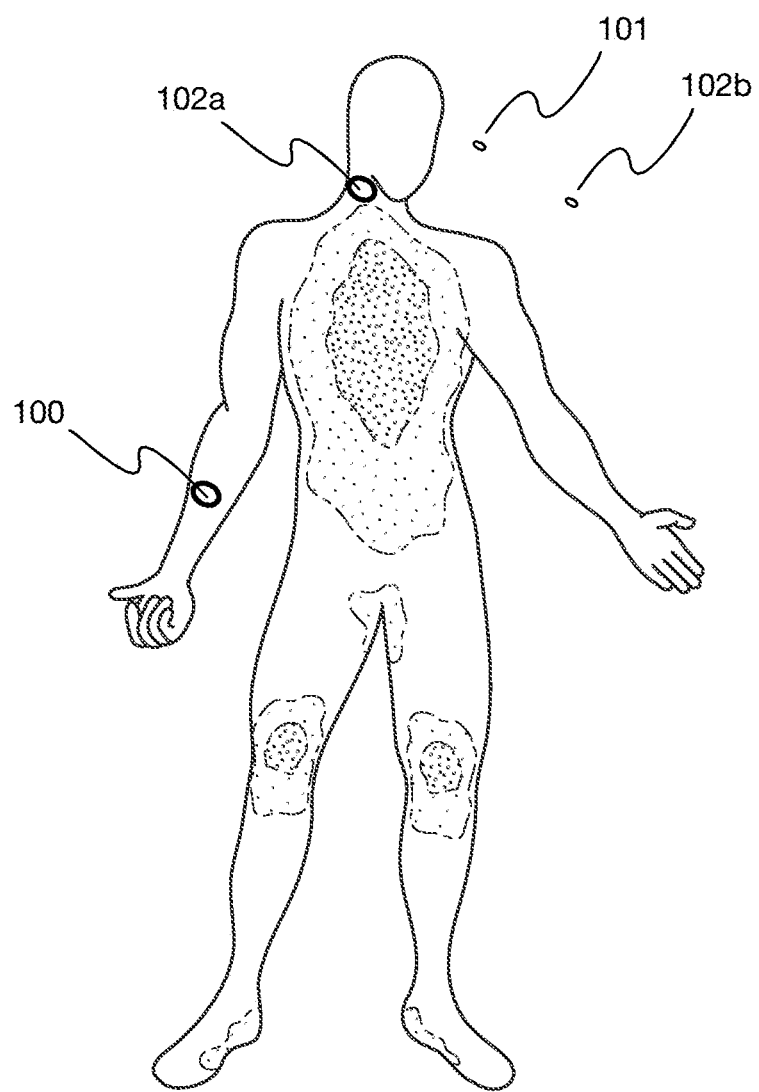
FIG. 1 illustrates temperature differential in a human body, wherein the apparatus may be applied to any portion of the human body.

According to at least one embodiment of the invention, which may be worn anywhere on the human body as shown in FIG. 1, an apparatus 100 (as shown in FIGS. 2B and 3B) that causes a beneficial effect at least by providing phototherapy to a human body and for example in some embodiments as a result of elevating copper peptide, including activation of stem cells, improvements in energy, elevation of antioxidants, reduction in inflammation, management of pain, improvements in stamina, elevation of collagen production, improved wound healing.

According to at least one embodiment, the invention provides apparatus 100 comprising biomolecular components that may include molecules associated with building-up of energy. In one or more embodiments, biomolecular components may include a Left-Handed molecule such as, for example, an amino acid. In at least one embodiment, the apparatus may include a structure that may be used for promoting the flow of energy (electrons) within a human body so as to improve physical strength of a user, wherein the structure may include a Left-Handed molecule such as, for example, an amino acid.

By way of at least one embodiment, the left-handed material-containing apparatus includes materials specifically pre-selected because such materials may interact with the infrared heat (light) being emitted by the human body, and thus stimulate the materials inside the patch causing them to reflect specific wavelengths of light back to the body (phototherapy). In one or more embodiments, a packet of photons, such as one packet, may stimulate a human receptor, such that only very small amounts of energy are required to cause the photobiomodulation effect.

By way of at least one embodiment, the Left-Handed amino acids that are suitable for use in at least one embodiment of the invention may include, for example, L-Glutamine, L-Arginine, L-Ornithine, L-Carnitine, L-Taurine, L-Tryptophan, L-Glycine, etc. Preferably, the amino acids used in at least one embodiment of the invention are orthomolecular amino acids.

In one or more embodiments, the Left-Handed molecule is an amino acid found in nature. In one or more embodiments, the Left-Handed molecule is an amino acid synthesized by man. In at least one embodiment, amino acids may include, but not limited to, L-Alanine, L-Arginine, L-Aspargine, L-Aspartic Acid, L-Carnitine, Acetyl-L-Carnitine, L-Carnitine L-Tartrate, L-Carnitine Magnesium Citrate, L-Citrulline, L-Cysteine, L-Cystine, L-GABA, L-Glutamic Acid, L-Glutamine, Glutathione Peroxidase, L-Glycine, L-Histidine, Hydroxyglutamic Acid, Hydroxyproline, L-Isoleucine, L-Leucine, Norleucine, L-Lysine, L-Methionine, L-Ornithine, L-Valine, L-Phenylalanine, L-Proline, L-Serine, L-Taurine, L-Threonine, L-Tryptophan, L-Tyrosine, other forms of Carnitine, etc. In at least one embodiment, the amino acids may be grouped with one or more of the above amino acids. In some embodiments, the Left-Handed molecules may include a synthetic L-sugar (L-glucose) or other synthetic levo-rotatory molecule known to one skilled in the art.

According to at least one embodiment of the invention, the Left-Handed molecule may be employed in a variety of ways. In one example, the biomolecular components including the Left-Handed molecules may be used in the form of a liquid, with said liquid being sprayed or similarly applied to a substrate. In another example, the biomolecular components including the Left-Handed molecule may be used in the form of a solid, such as a powder, with said powder being mixed with a binder such as latex rubber, silicone rubber, epoxy, wax or the like, with the powdered amino acid and binder being applied to a substrate.

According to at least one embodiment, the invention may include a structure that includes a plurality of Left-Handed molecules. In one or more embodiments, more than one kind of Left-Handed molecules may be utilized in a structure. In one example, a structure in which L-glutamine may be applied to a single substrate, followed by the layering of a second amino acid such as L-Arginine to a second substrate, with both treated substrates forming part of the completed structure of at least one embodiment of the invention. In one or more embodiments, portions of L-Glutamine and L-Arginine may be mixed together, and then applied in the form of a liquid or powder to a single substrate. In another example, two or more L amino acids may be applied to the same substrate.

At least one embodiment of the invention may include one or more additives for the Left-Handed molecules. The examples of additives may include, but not limited to Glycerin, d-calcium pantothenate, sorbitol, propylparaben, potassium sorbate, methylparaben, Colloidal Copper and/or Collodial Gold, etc.

One or more embodiments of the invention provide an apparatus including a sealed enclosure, wherein the sealed enclosure may enclose biomolecular components (e.g., Left-Handed molecules), for example for providing phototherapy to the human body, and one or more substrates for the biomolecular components. The sealed enclosure may be made of a material, for example, but not limited to a polyester film sheet (e.g., manufactured by GBC, a thermal laminating film, etc.), a plastic film (e.g., polyethylene, polypropylene, ABS, plexiglass, Lexan, PVC, etc.), etc. In at least one embodiment, the polyester film sheet and/or the plastic film may be utilized in construction of the apparatus of the invention. In one or more embodiments the sealed enclosure may be made of a light polarizing film. In other embodiments the sealed enclosure may be made of a linear low-density film.

According to at least one embodiment of the invention, the sealed enclosure may not react (i.e., chemically, etc.) with biomolecular components (e.g., Left-Handed molecules) of the invention. In one or more embodiments, the sealed enclosure may be capable of being sealed to a predefined fashion to keep the Left-Handed molecules in a liquid state. In one or more embodiments, the sealed enclosure may be capable of being sealed in a predefined fashion to protect the Left-Handed molecules from ambient environmental conditions.

By way of at least one embodiment, examples of methods of sealing plastic films may include, for example, pressure sensitive or thermally sensitive adhesives, ultrasonic sealing, etc.

According to at least one embodiment, the invention provides an apparatus that includes a container, for example a sealed plastic enclosure that encloses biomolecular components, for example for providing phototherapy to a human body, and one or more substrates for the biomolecular components, wherein the apparatus further includes one or more gem stones (e.g., Jade, powdered jade, etc.).

In one or more embodiments, Jade may be used for decorative purposes, and for the practice of the invention. Jade (or other gem stones) may be incorporated into the invention in either gem stone form, or in powdered form. If Jade is incorporated in stone form, then the apparatus of at least one embodiment of the invention may be embodied as decorative items such as jewelry, etc. If Jade is incorporated in powdered form, then the Jade powder may be added to the Left-Handed molecules. The Jade may also be added in other parts of the devices of the invention so as to make the apparatus practical for use.

According to one or more embodiments, the invention provides one or more physical structural settings for holding one or more components of apparatus 100. In one or more embodiments, that the one or more physical structural settings may hold biomolecular components, for example for providing phototherapy to the human body, one or more substrates for the biomolecular components, and one or more gem stones (e.g., Jade, powdered jade, etc.).

According to at least one embodiment, apparatus 100 may be in one or more of a plurality of wearable objects, for example, but not limited to dermal patches, bracelets, pendants, support pads, shirts, socks, foot inserts, etc.

According to at least one embodiment, the invention may include a patch having an adhesive (e.g., medical grade adhesive). In one or more embodiments, the invention may include a single patch. In one or more embodiments, the invention may include a plurality of patches. In one embodiment, the patch may be constructed in layers made of plastic film or light polarizing film, polyester fabric as a substrate, Water, L-Carnitine, Glycerin, d-calcium pantothenate, sorbitol, propylparaben, potassium sorbate, and methylparaben. In another embodiment, the patch may be constructed in layers made of a plastic film or a light polarizing film as an enclosure, a polyester fabric as a substrate.

By way of one or more embodiments, apparatus 100 of the present invention may be embodied as jewelry items, then the apparatus may be mounted in virtually any jewelry setting that is already commercially available, provided that the setting does not interfere in any way with the operation of apparatus 100 of the present invention. In at least one embodiment, apparatus 100 of the invention may be embodied as a band aid or as a patch (transdermal or non-transdermal), such that a setting would not be needed. In at least one embodiment, apparatus 100 of the invention may be completely sealed, thereby the Left-Handed molecules may not make direct contact with a user of apparatus 100. In addition, in at least one embodiment, the Left-Handed molecules may not enter into body of the user.

In one or more embodiments, apparatus 100 of the invention having Left-Handed molecules may be manufactured with the following specifications:

One or more embodiments of the invention provide a method for placing apparatus 100 on a predetermined location of a human body or into a human body, wherein apparatus 100 produces a beneficial effect when placed on the human body or into the human body, wherein apparatus 100 at least provides phototherapy to the human body for producing the beneficial effect. The apparatus 100 may include, for example, patch, bracelet, necklace, anklet, etc.

One or more embodiments of the invention provide methods for placing apparatus 100 into proximity of a human body. In one example, apparatus 100 may be attached to pendants and allowed to be placed into proximity of the human body. In another example, apparatus 100 may be embodied in "Band Aid" style or "Patch" style, with a medical grade adhesive being applied to the device to make it suitable for use with human beings.

In at least one embodiment, apparatus 100 (e.g., dermal patch) having Left-Handed molecules may be placed at an electrically POSITIVE point on the body. Positive and Negative points on the body have been metered and the locations thereof are known.

Furthermore, in one or more embodiments, apparatus 100 (e.g., dermal patch) may be placed at known acupuncture points. For example, in one or more embodiments, apparatus 100 having Left-Handed molecules (e.g., POSITIVE dermal patch) may be placed at a YANG (positive) point.

According to at least one embodiment of the invention illustrated in FIG. 2A, apparatus 100 may cause a beneficial effect (e.g., improvement in strength/stamina, relief from a pain, etc.), for example by providing phototherapy to a human body, and for example in some embodiments as a result of elevating copper peptide, including activation of stem cells, improvements in energy, elevation of antioxidants, reduction in inflammation, management of pain, improvements in stamina, elevation of collagen production, improved wound healing and may include a single layer fabric substrate 110 for retaining biomolecular components.

FIG. 2B illustrates a sealed single layer fabric substrate that retain the biomolecular components.

According to at least one embodiment of the invention illustrated in FIG. 3A, apparatus 100 that causes beneficial effect (e.g., improvement in strength/stamina, relief from a pain, etc.), for example, by providing phototherapy to a human body, and may include two layers of fabric substrate 120 for retaining biomolecular components including. Apparatus 100, as illustrated, may be fabricated in accordance with the principles as described here in the preceding disclosure.

FIG. 3B illustrates a sealed multi-layer fabric substrate that retain the biomolecular components, according to one or more embodiments of the invention.

According to at least one embodiment of the invention illustrated in FIG. 4, a patch 400 may include apparatus 100 for causing a beneficial effect (e.g., improvement in strength/ stamina, relief from a pain etc.) for a human body, for example by providing phototherapy to a human body. In one or more embodiments, one or more portions of patch 400 may include medical grade adhesive for enabling attachment of patch 400 to human skin surface.

According to at least one embodiment of the invention illustrated in FIG. 5, a bracelet 500 may include apparatus 100 for causing a beneficial effect (e.g., improvement in strength/stamina, relief from a pain, etc.) for a human body, for example by providing phototherapy to a human body. In one or more embodiments, bracelet 500 may also include a gem stone (not shown in FIG. 5).

According to at least one embodiment of the invention illustrated in FIG. 6, a ring 600 may include apparatus 100 for causing a beneficial effect (e.g., improvement in strength/ stamina, relief from a pain, etc.) for a human body, for example by providing phototherapy to a human body. In one or more embodiments, ring 600 may also include a gem stone 610.

According to at least one embodiment of the invention illustrated in FIG. 7, a watch 700 may include apparatus 100 for causing a beneficial effect (e.g., improvement in strength/ stamina, relief from a pain, etc.) for a human body, for example by providing phototherapy human body. By way of one or more embodiments, the system may include a phototherapy device system. In at least one embodiment, the system is applied to the subject's body to provide a beneficial effect for the subject selected from a group consisting of activation of stem cells, an improvement in energy, an elevation of antioxidants, a reduction in inflammation, an elevation of collagen production, an improvement in wound healing, an increase in strength, an increase in stamina, a relief from pain and an improvement in strength endurance.

FIG. 8A illustrates a system that includes a first layer that may include one or more of a transdermal patch and a non-transdermal patch, and a second layer with one or more of at least one Left-Handed material-containing apparatus coupled on top of the first layer, according to one or more embodiments of the invention.

As shown in FIG. 8A, at least one embodiment of the invention includes a system 800 that includes a first layer with a patch 802. In at least one embodiment, patch 802 may be one or more of a transdermal patch and a non-transdermal patch. In one or more embodiments, the patch 802 consists essentially of copper peptide GHK-Cu, such that the patch 802 may deliver the copper peptide GHK-Cu into the subject's body 804. In at least one embodiment of the invention, the system 800 includes a second layer 100, such as the apparatus 100 that causes a beneficial effect, for example by providing phototherapy to a human body, illustrated in FIGS. 2A, 2B, 3A, 3B, 4, 5, 6 and 7.

In one or more embodiments of the invention, the second layer 100 is coupled to the first layer 802, wherein the second layer 100 includes the at least one Left-Handed material-containing apparatus applied to the subject's body 804. In one or more embodiments, the second layer may include a plurality of Left-Handed material-containing apparatuses simultaneously applied to the subject's body. In at least one embodiment, the apparatus and layers thereof may include one or more of organic and non-organic molecules.

In one or more embodiments, the at least one Left-Handed material-containing apparatus comprises at least one Left-Handed molecule comprising at least one Left-Handed organic molecule or at least one Left-Handed non-organic molecule or both at least one Left-Handed organic molecule and at least one Left-Handed non-organic molecule. By way of at least one embodiment of the invention, the at least one Left-Handed material-containing apparatus reflects or emits specific wavelengths of light that elevate levels of the copper peptide GHK-Cu in the subject's body. In one or more embodiments, the elevation of levels of the copper peptide GHK-Cu activates stem cells in the subject's body. For example, by way of at least one embodiment, the copper peptide may act as a signaling model to increase proliferation of stem cells. As such, by way of one or more embodiments, the decline of copper peptide in the subject's body, for example due to aging, may be improved by elevating or increasing the levels of the copper peptide using the phototherapy apparatus.

By way of one or more embodiments, the non-transdermal patch may include two phototherapy layers as a first phototherapy layer and a second phototherapy layer. In at least one embodiment, the first phototherapy layer and the second phototherapy layer are layered and coupled on top of each other, such that one layer of the two phototherapy layers is layered and coupled on top of a second layer of the two phototherapy layers. In one or more embodiments, the first phototherapy layer and the second phototherapy layer are layered and coupled as concentric rings. In at least one embodiment, via the two phototherapy layers, the non-transdermal patch reflects different wavelengths of light from each layer of the first phototherapy layer and the second phototherapy layer, therefore producing additional beneficial biological effects.

According to one or more embodiments, the phototherapy apparatus may deliver ingredients to the subject's body that compliment the function of GHK-Cu, via one or more patches or layers. In at least one embodiment, the ingredients may include minerals such as copper, zinc, selenium, magnesium and sulphur, wherein such ingredients support wound healing and thus provide an advantage to the subject's body.

By way of at least one embodiment, as shown in FIG. 8A, the second layer 100 is coupled on top of the first layer 802 that includes the patch 802.

FIG. 8B illustrates the system 800 that includes the first layer 802 with a patch, and the second layer 100 with one or more of at least one Left-Handed material-containing apparatus directly coupled to the first layer 802 side by side, according to one or more embodiments of the invention. In at least one embodiment of the invention, the patch may include one or more of a transdermal patch and a non-transdermal patch. For example, some ingredients that are beneficial as non-transdermal embodiments may be configured to encapsulate the ingredients so that they do not enter the skin, while other transdermal ingredients may be held is portions of the device that allow those ingredients to enter the skin. As shown in FIG. 8B, first layer 802 may be implemented with a non-transdermal ingredient that is not configured to enter the skin, while second layer 100 is implemented with a transdermal ingredient that is configured to enter the skin, or visa versa wherein first layer 802 has a transdermal ingredient and is configured to allow that ingredient to enter the skin while second layer 100 has the non-transdermal ingredient. Any other embodiment of the invention may also contain transdermal portions depending on the desired application.

FIG. 8C illustrates the system 800 that includes the first layer 802 with a patch, and the second layer 100 with one or more of at least one Left-Handed material-containing apparatus indirectly coupled to the first layer 802 side by side, according to one or more embodiments of the invention. In at least one embodiment of the invention, the patch may include one or more of a transdermal patch and a non-transdermal patch.

FIG. 8D illustrates the system 800 that includes the first layer 802 with a patch, and the second layer 100 with one or more of at least one Left-Handed material-containing apparatus layered as concentric rings, according to one or more embodiments of the invention. In at least one embodiment of the invention, the patch may include one or more of a transdermal patch and a non-transdermal patch. In at least one embodiment of the invention, the placement of the first layer 802 and the second layer 100 as concentric rings may be switched such that the first layer may fit inside the second layer or vice versa, and such that the first layer and the second layer include a common center with an equal distance apart all the way around.

In one or more embodiments of the invention, as shown in FIG. 8C, the first layer 802 is coupled to the second layer 100 side by side, wherein the first layer 802 is separated from the second layer 100, such that the first layer 802 attaches to a first portion of the subject's body 804 and the second layer 100 attaches to a second portion of the subject's body 804.

FIG. 9A illustrates an example of a patch including the system that causes a beneficial effect within a human body, according to at least one embodiment of the invention.

According to at least one embodiment of the invention, FIG. 9A shows the patch 400, as illustrated in FIG. 4 and as discussed above, that may include system 800, to cause a beneficial effect (e.g., improvement in strength/stamina, relief from a pain etc.) for a human body, for example by providing phototherapy to a human body, such as the subject's body 804.

FIG. 9B illustrates an example of a bracelet including a system that causes a beneficial effect within a human body, according to at least one embodiment of the invention.

According to at least one embodiment of the invention, FIG. 9B shows the bracelet 500, as illustrated in FIG. 5 and as discussed above, that may include system 800, to cause a beneficial effect (e.g., improvement in strength/stamina, relief from a pain, etc.) for a human body, for example by providing phototherapy to a human body, such as the subject's body 804.

FIG. 9C illustrates an example of a ring including a system that causes a beneficial effect within a human body, according to at least one embodiment of the invention.

According to at least one embodiment of the invention, FIG. 9C shows the ring 600, as illustrated in FIG. 6 and as discussed above, that may include system 800, to cause a beneficial effect (e.g., improvement in strength/stamina, relief from a pain, etc.) for a human body, for example by providing phototherapy to a human body, such as the subject's body 804.

FIG. 9D illustrates an example of a watch including a system that causes a beneficial effect within a human body, according to at least one embodiment of the invention.

According to at least one embodiment of the invention, FIG. 9D shows the watch 700, as illustrated in FIG. 7 and as discussed above, that may include system 800, to cause a beneficial effect (e.g., improvement in strength/stamina, relief from a pain, etc.) for a human body, for example by providing phototherapy to a human body, such as the subject's body 804.

According to at least one embodiment of the invention, the first layer 802 may deliver chemicals and nutrients to the subject's body 804, and the second layer 100 may not deliver such chemicals and nutrients to the subject's body 804, for example when applied simultaneously.

FIG. 10A illustrates a patch, such as the non-transdermal patch, with at least one ball or bead located underneath the patch at an outer surface of the patch, according to one or more embodiments of the invention. FIG. 10B illustrates a patch, such as the non-transdermal patch, with at least one ball or bead located between layers of the patch, according to one or more embodiments of the invention. As shown in FIG. 10A and FIG. 10B, the patch, such as the non-transdermal patch, may include at least one ball or bead 1055. In at least one embodiment, the at least one ball or bead 1055 may be or may include plastic. In one or more embodiments, the at least one ball or bead 1055 may be located at the bottom of the non-transdermal patch as shown in FIG. 10A, such as underneath the non-transdermal patch at an outer surface of the non-transdermal patch. For example, in one or more embodiments, the at least one ball or bead 1055 may be located at an outer surface of first layer 802 or second layer 100. In at least one embodiment of the invention, the at least one ball or bead 1055 may be located underneath the non-transdermal patch, wherein the at least one ball or bead directly or indirectly contacts the user's skin, such as at user's body 804. In one or more embodiments, the at least one ball or bead 1055 may be located between layers of the non-transdermal patch, such as for example between the first layer 802 and the second layer 100 of the non-transdermal patch. By way of at least one embodiment, the at least one ball or bead 1055 may stimulate the user's skin with mild pressure. In one or more embodiments of the invention, each of the at least one ball or bead may include a diameter of 0.218 inches, 0.187 inches, 0.156 inches or 0.182 inches. According to one or more embodiments of the invention, the ball or bead 1055 may stimulate specific points on the user's skin to provide additional beneficial biological effects, such as to mobilize stem cells of the user.

By way of one or more embodiments, the phototherapy apparatus may stimulate the skin with specific wavelengths of light to elevate the copper peptide GHK-Cu, such that the copper peptide GHK-Cu may effectively stimulate the natural healing process in the subject's body. See "Experimental Study of LiveWave, Inc. X-39 patches", Summary and report, The Centre for Biofeld Sciences, Integrated Health, 23 Nov. 2018; incorporated herein by references in its entirety.

A pilot study was conducted with forty experimental and five control voluntary subjects who were studied before and after wearing the patch for a period of six weeks, using cutting edge non-invasive screening technologies such as biofield imaging, electro photonic imaging and electro-interstitial screening. Such devices were used to extract a broad spectrum of data ranging from physical, energetic and emotional aspects of the subject's body non-invasively and efficiently. Statistical analysis of data revealed a highly significant increase (p<0.0001) in overall energy of subjects' biofield and significant improvement (p<0.05) in the symmetrical distribution of energy between the organs of the subjects. Also, a significant improvement (p<0.05) in vital energy after using the patches for 6 weeks showed positive changes in the biofield of the subjects.

Forty-five subjects aged between 40 to 65 years were randomly selected to take part in the study of the efficacy of the patch, out of which forty subjects were in the experimental group and five subjects served as control group.

The data collection was done in three phases starting with the baseline on the day before the subject start wearing the patches, seconds set of scans were taken after 3 weeks and the final scans were done after 6 weeks from the baseline scan date. The patches were placed at the base of the back of the neck where C7 vertebrae protrude. The subjects were instructed to wear a new patch every day for 12 hours during the daytime for 6 weeks.

The pilot study demonstrates a statistically significant improvement in the subjects biofield from using the patch. The statistical analysis revealed a highly significant improvement (p<0.0001) in overall energy of the person and significant improvement (p<0.05) in the symmetrical distribution of energy over different organs. From the above, it is concluded wherein the patch is effective in elevating the overall energetic vitality of the biofield and the body and also boosting the self-healing mechanisms.

According to at least one embodiment of the invention, the non-transdermal patch is sealed such that none of the substances in the patch actually penetrate the skin. In one or more embodiments, this allows for consistent patch promotion of the light flow throughout the time the patch is worn. The patch, according to at least one embodiment, stimulates the copper peptide GHK-Cu. By way of one or more embodiments, the patch may be placed on the back, such as at GV14, Du-14 or Dao, at a meeting point of the governing vessel with all of the Yang meridians. In at least one embodiment, the patch may be placed at a point on the lower abdomen, at CV-6, Ren 6, or Qi Hai.

See "Metabolic Implications of the LiveWave X39 Patch", to Connor et al., incorporated herein by reference in its entirety.

This study explores the metabolic implications and physiologic results of wearing the patch over the period of one week. Measures were taken at baseline, 24 hours and at 7 days of wearing the patch. A sample of convenience of 15 subjects made up of both men and women aged 40-65 were selected to participate in this study. In this study, the initial baseline readings were taken, and then the patch was applied. The participant will be asked to wear the patch 12 hours each day. The participant removed the patch at night and a fresh patch was applied each morning prior to 8 am. The patch was worn for a minimum of 1 hour before the additional data measures were taken. Patches were worn for a total of 7 days. Data taking with the patch applied was done on day one, day two and day seven. This study focused on the metabolic impact of patch usage, with half the participants using the CV6 point and half using the GV14 point.

Amino acids and neurotransmitters play a critical role in the health and wellbeing of individuals. If an individual's amino acid and neurotransmitter production is broken, the individual cannot maintain body health for long. The number of statistically significant changes demonstrated in this study shows the powerful impact, which may be created by the use of phototherapy products, and the clear positive changes produced by the application of the specific non-transdermal patch. Key findings are Glutamate and Histamine as they show a distinct anti-inflammatory trend produced by the patch.

Of note, importantly, the amino acids Glycine and Glutamate, which are used for example in the process to form Glutathione in a transsulfuration pathway, both showed a drop off at a level of significance, shown in Table 1 below.

TABLE 1

| Glu | Day 1 to Day 2 | −2.00 | 6.71 | 0.2674 |
| Glu | Day 2 to Day 7 | −3.82 | 6.73 | 0.0453 |
| Glu | Day 1 to Day 7 | −5.82 | 10.37 | 0.0475 |
| Gly | Day 1 to Day 2 | −72.54 | 117.73 | 0.0317 |
| Gly | Day 2 to Day 7 | 34.67 | 107.20 | 0.2308 |
| Gly | Day 1 to Day 7 | −37.87 | 83.70 | 0.1016 |

For example, Glutahione is part of the body system that supports reduction of inflammation pathways in a unique aspect. For example, it specifically acts from the liver to detoxify the blood. As such, for example, it clears heavy metals from the body rather than acting as an anti-inflammatory agent directly. A decrease in the materials that produce the glutathione as the result of patch usage means that more glutathione is being made. For example, this results in higher availability of the glutathione in the blood and allows the body to clear more damaging material faster.

FIG. 11 illustrates an increase in production of Glutathione as a result of using the patch, providing an improved anti-inflammatory response, via a decrease in the materials that produce the Glutathione, according to one or more embodiments of the invention. By way of one or more embodiments, Glutamate and Glycine both drop to produce Glutathione. In at least one embodiment, Glutathione is a critical part of the anti-inflammatory pathway. For example, in at least one embodiment of the invention, Glycine combines with Glutamate to produce Glutathione through the transsulfuration pathway. In one or more embodiments of the invention, as shown in Table 1 above, between day one and day two, Glycine drops at a level of significance and then starting day two the Glutamate drops at a level of significance. As such, for example, between day one and day seven, Glutathione is produced at a higher level and thus produces an improved anti-inflammatory response, reducing inflammation, shown in FIG. 11.

For example, fifteen subjects were tested, and as shown in Table 2 below, the sample obtained from day 7 shows seven of the fifteen subjects with levels of Glutathione increasing.

TABLE 2

| Subject | Glutathione Levels | | | |
|---|---|---|---|---|
| 1 | Day 1 to Day 7 | 6.20 | 6.00 | 4.21 |
| 2 | Day 1 to Day 7 | 0.92 | 0.48 | 0.61 |
| 3 | Day 1 to Day 7 | 0.78 | 1.39 | 4.19 |
| 4 | Day 1 to Day 7 | 1.52 | 3.74 | 6.41 |
| 5 | Day 1 to Day 7 | 1.16 | 1.30 | 2.78 |
| 6 | Day 1 to Day 7 | 1.75 | 2.15 | 1.45 |
| 7 | Day 1 to Day 7 | 0.17 | 0.77 | 0.16 |
| 8 | Day 1 to Day 7 | 1.49 | 0.58 | 1.88 |
| 9 | Day 1 to Day 7 | 0.76 | 0.70 | 2.42 |
| 10 | Day 1 to Day 7 | 0.68 | 0.41 | 2.26 |
| 11 | Day 1 to Day 7 | 0.64 | 1.44 | 0.69 |
| 12 | Day 1 to Day 7 | 0.99 | 1.43 | 1.11 |

TABLE 2-continued

| Subject | | Glutathione Levels | | |
|---|---|---|---|---|
| 13 | Day 1 to Day 7 | 1.21 | 1.49 | 0.98 |
| 14 | Day 1 to Day 7 | 0.94 | 0.80 | 1.01 |
| 15 | Day 1 to Day 7 | 0.97 | 0.99 | 1.15 |

The study also included metabolic testing and physiological testing. Metabolic testing consisted of one 10 am urine taken at baseline/day one, day two and day seven. Saliva testing consisted of a six swabs taken in one day at baseline/day one, day two and seven. All study participants had the following physiological testing done at base line, 24 hours and 7 days: Six minute recordings of EKG, pulse, respiration, heart rate variability (HRV), temp, blood volume pulse, galvanic skin response, and 2 EMG (muscle) leads (one on each shoulder area). At baseline testing, participants were checked for any allergic reactions to the adhesive patches. Fresh adhesive patches were used for each person tested. Data from questionnaires were collected on standard answer sheets and scored. All questionnaires parameters were summarized in terms of means and standard deviation, stratified by assessment time point. Changes between assessment time points were evaluated using a paired t-test or nonparametric Wilcoxon Signed Rank test. All physiology parameters were summarized in terms of means and standard deviation, stratified and across the 6 study epochs. Changes from pre- to post patch administration were evaluated using a paired t-test. Normal probability plots were examined to verify the distribution assumptions. All reported P-values are two-sided and P<0.05 was used to define statistical significance. All metabolic parameters were summarized in terms of means and standard deviation, stratified by assessment time point. Changes from day 1 (pre-patch) to day 2, day 2 to day 7, and day 1 to day 7 were evaluated using a paired t-test or nonparametric Wilcoxon Signed Rank test. Cortisol levels were obtained at 8 am, 12 pm, 4 pm, Bpm and 12 am. DHEAS levels were collected at 8 am, Bpm and 12 am. The area under the curve (AUC) for Cortisol and DHEAS levels over the data collection periods was calculated using the trapezoid rule. AUC levels were summarized in terms of means and standard deviations, stratified by assessment time point. Changes between assessment time points were evaluated using a paired t-test or Wilcoxon signed rank test.

The study included five men and 10 women with a mean age of 61.9±9.3 years. The results of the testing is summarized with tables below:

TABLE 3

Demographics (N = 15):

| | N (%) |
|---|---|
| Gender | |
| Female | 10 (67%) |
| Male | 5 (33%) |
| Age (yrs), means ± SD | 61.9 ± 9.3 |

As shown from Table 3 above, the experiment included five men and 10 women with a mean age of 61.9±9.3 years.

TABLE 4

Changes in Arizona Integrative Outcome Scale, Visual Analogue Scale (AIOS-VAS) instrument scores from Consent to 1.2, Consent to day 2, and Consent to day 7 assessments:

| | Mean Change | SD | p-value |
|---|---|---|---|
| Change from 1.1 to 2 | 7.6 | 15.3 | 0.0877 |
| Change from 1.1 to 7 | 15.3 | 20.6 | 0.0151 |

For example, the AIOS-VAS looks at the overall wellness of an individual. As shown above, for example, there was a clear shift established by the second day of testing, which increased to significance by day 7 showing clear overall improvement in the feelings of vitality and wellness.

TABLE 5

Changes in WAISIII instrument scores from day 1 to day 7:

| | Outcome | Mean Change | SD | p-value |
|---|---|---|---|---|
| Change from Day 1 to Day 7 | # Short | 1.1 | 2.4 | 0.0872 |
| | # Mid | 0.8 | 2.9 | 0.3008 |
| | # Long | 1.1 | 3.2 | 0.2170 |

For example, the WAIS III is an intelligence test that includes a standard memory test. For example, memory is a common issue for people above age 45. As shown above, for example, there was a clear improvement in short-term memory by day 7. For example, it is likely that this would get more significant with a larger group of people and a longer intervention period. As shown above, for example, there was an improvement in both mid and long-term memory as well.

TABLE 6

Changes in modified Pittsburg Sleep Quality Index (PSQI) instrument scores from day 1 to day 2 and from day 1 to day 7:

| | Mean Change | SD | p-value |
|---|---|---|---|
| Change from Day 1 to Day 2 | −1.0 | 1.3 | 0.0676 |
| Change from Day 1 to Day 7 | −3.0 | 2.9 | 0.0522 |

The PSQI was used to look at sleep, which for example is also a common issue once past the age of 45. As shown above, the questionnaire showed an immediate strong shift the first night, and a significant shift by day 7. For example, this is particularly important as sleep strongly affects the subject's health and wellbeing.

TABLE 7

Change from day 1 (pre-patch) to day 2, day 2 to day 7, and day 1 (pre-patch) to day 7:

| Marker | Change | Mean Change | SD | p-value |
|---|---|---|---|---|
| Alanine | Day 1 to Day 2 | −20.17 | 36.89 | 0.0526 |
| Cystine | Day 2 to Day 7 | −16.07 | 23.86 | 0.0206 |
| Epinephrine | Day 1 to Day 2 | −2.09 | 3.08 | 0.0197 |
| Epinephrine | Day 2 to Day 7 | 1.59 | 2.94 | 0.0552 |
| GABA | Day 1 to Day 7 | −0.73 | 1.50 | 0.0818 |
| Glutathione | Day 2 to Day 7 | −3.82 | 6.73 | 0.0453 |
| Glutathione | Day 1 to Day 7 | −5.82 | 10.37 | 0.0475 |
| Glycine | Day 1 to Day 2 | −72.54 | 117.73 | 0.0317 |
| HCys2 | Day 1 to Day 2 | 0.35 | 0.55 | 0.0296 |

TABLE 7-continued

Change from day 1 (pre-patch) to day 2, day 2 to day 7, and day 1 (pre-patch) to day 7:

| Marker | Change | Mean Change | SD | p-value |
|---|---|---|---|---|
| Histamine | Day 1 to Day 2 | −46.32 | 75.35 | 0.0320 |
| Histamine | Day 1 to Day 7 | −46.64 | 49.35 | 0.0026 |
| Histamine (free) | Day 1 to Day 2 | −9.24 | 20.20 | 0.0981 |
| Hydroxylysine | Day 1 to Day 7 | −0.80 | 1.75 | 0.0992 |
| Leucine | Day 1 to Day 2 | −4.84 | 7.84 | 0.0313 |
| Normetanephrine | Day 2 to Day 7 | −13.06 | 23.32 | 0.0479 |
| PEA Phenylethylamine | Day 1 to Day 7 | −0.59 | 1.12 | 0.0589 |
| Phenylalanine | Day 2 to Day 7 | 6.33 | 10.94 | 0.0418 |
| Tryptophan | Day 2 to Day 7 | −10.81 | 18.55 | 0.0406 |
| Alpha-aminobutyric acid | Day 1 to Day 7 | −8.90 | 13.79 | 0.0256 |
| Alpha-aminobutyric acid | Day 2 to Day 7 | −5.29 | 7.79 | 0.0198 |

For example, amino acids and neurotransmitters play a critical role in the health and wellbeing of individuals. For example, if an individual's amino acid and neurotransmitter production is broken, the individual may not maintain body health for long. For example, the number of statistically significant changes demonstrated in this study shows the powerful impact that may be created by the use of phototherapy products and the clear positive changes produced by the application of this specific non-transdermal patch, by way of one or more embodiments of the invention. Key findings are Glutamate and Histamine as they show a distinct anti-inflammatory trend produced by the patch.

Of note, importantly, the amino acids Glycine and Glutamate, which are used in the process to form Glutathione in a transsulfuration pathway, both showed a drop off at a level of significance. For example, glutathione is part of the body system that supports reduction of inflammation pathways in a unique aspect. For example, it specifically acts from the liver to detoxify the blood, as discussed above. A decrease in the materials that produce the glutathione as the result of patch usage means that more glutathione is being made. This results in higher availability of the glutathione in the blood and allows the body to clear more damaging material faster. This supports the overall reduction in inflammation, which is demonstrated in the data results.

TABLE 8

Change from pre-patch to last-patch (day 7) of High Frequency (HF), a ratio of Low Frequency to High Frequency (LF/HF) of number of pairs of successive NN (RR) intervals that differ by more than 50 ms (NN50), proportion of NN50 divided by the total number of NN (R-R) intervals (PNN50), Power, root mean square of the successive differences (RMSSD), and very low frequency (VLF), stratified by Epoch (1-6):

| Source | Outcome | Epoch | Mean Change | SD | p-value |
|---|---|---|---|---|---|
| EKG | SDNN | 2 | −42.89 | 82.71 | 0.06430 |
| BVP | HF | 5 | −1085.13 | 2038.55 | 0.05830 |
| BVP | NN50 | 1 | −3.13 | 5.34 | 0.03950 |
| BVP | NN50 | 2 | −2.13 | 4.12 | 0.06470 |
| BVP | NN50 | 3 | −1.73 | 2.89 | 0.03580 |
| BVP | NN50 | 5 | −2.73 | 3.03 | 0.00360 |
| BVP | PNN50 | 1 | −0.05 | 0.08 | 0.03820 |
| BVP | PNN50 | 2 | −0.03 | 0.07 | 0.06880 |
| BVP | PNN50 | 3 | −0.03 | 0.04 | 0.04290 |
| BVP | PNN50 | 5 | −0.04 | 0.04 | 0.00360 |
| BVP | RMSSD | 5 | −21.13 | 36.49 | 0.04160 |

TABLE 8-continued

Change from pre-patch to last-patch (day 7) of High Frequency (HF), a ratio of Low Frequency to High Frequency (LF/HF) of number of pairs of successive NN (RR) intervals that differ by more than 50 ms (NN50), proportion of NN50 divided by the total number of NN (R-R) intervals (PNN50), Power, root mean square of the successive differences (RMSSD), and very low frequency (VLF), stratified by Epoch (1-6):

| Source | Outcome | Epoch | Mean Change | SD | p-value |
|---|---|---|---|---|---|
| BVP | SDNN | 5 | −19.42 | 27.08 | 0.01480 |
| BVP | VLF | 5 | −382.47 | 426.65 | 0.00370 |

TABLE 9

Change from pre-patch to last-patch (day 7) of HF, LF/HF NN50, PNN50, Power, RMSSD, and VLF, across all 6 Epochs:

| Source | Outcome | Mean Change | SD | p-value |
|---|---|---|---|---|
| EKG | HF | −1115.01 | 28492.47 | 0.7113 |
| EKG | LF | 14424.43 | 104293.22 | 0.1929 |
| EKG | LF/HF | 0.28 | 1.31 | 0.0487 |
| BVP | HF | −786.72 | 3852.92 | 0.0559 |
| BVP | LF | 205.48 | 4414.61 | 0.6599 |
| BVP | LF/HF | −0.08 | 5.93 | 0.9004 |
| BVP | NN50 | −1.96 | 3.80 | <.0001 |
| BVP | PNN50 | −0.03 | 0.06 | <.0001 |
| BVP | RMSSD | −21.78 | 76.48 | 0.0083 |
| BVP | SDNN | −18.60 | 63.27 | 0.0065 |

TABLE 10

Change from pre-patch to last-patch (day 7) of blood volume pulse-heart rate (BVP-HR), electromyography (EMG), Skin-Condition, Temperature and Respiratory Rate for Average, Mode, and Area, stratified by Epoch (1-6):

| Source | Outcome | Epoch | Mean Change | SD | p-value |
|---|---|---|---|---|---|
| BVPHR | Average | 2 | 4.51 | 7.83 | 0.0426 |
| BVPHRMaxMin | Average | 5 | −2.23 | 3.13 | 0.0153 |
| BVPHRMaxMin | Mode | 1 | −1.18 | 2.17 | 0.0533 |
| BVPHRMaxMin | Mode | 2 | −0.73 | 1.57 | 0.0917 |
| EKGHRMaxMin | Mode | 6 | −33.34 | 67.42 | 0.0871 |
| RespRate | Mode | 1 | 1.92 | 4.03 | 0.0868 |

TABLE 11

Change from pre-patch to last-patch (day 7) of BVP-HR, EMG, Skin-Condition, Temperature and Respiratory Rate for Average, Mode, and Area, across all 6 Epochs:

| Source | Outcome | Mean Change | SD | p-value |
|---|---|---|---|---|
| BVPHR | Average | 2.54 | 8.31 | 0.0047 |
| BVPHR | Mode | 2.31 | 9.60 | 0.0249 |
| BVPHRMaxMin | Average | −1.67 | 5.50 | 0.0049 |
| EMG | Average | −39.44 | 124.62 | 0.0035 |
| EMG | Mode | −38.45 | 128.72 | 0.0057 |
| EMG | Area | −2366.63 | 7477.30 | 0.0035 |

As shown above, reduction in blood pressure and improved muscle relaxation are consistent changes that are present in the physiology data. For example, the study importantly shows greater flexibility in HRV in the over age 60 population.

As shown above, by way of one or more embodiments, the patch provides improvement in blood pressure and shows the impact of the metabolic changes shown in amino acid production. Key findings are Glutathione and Histamine results as they show a distinct anti-inflammatory trend produced by the patch, according to at least one embodiment. For example, such a result is further confirmed when looking at Glycine and Glutamate in combination, wherein they are used in the metabolic processes to form Glutathione through the transsulfuration pathway. Since both showed a drop off at a level of significance, this importantly shows that they are being used for the purpose of the production of Glutathione, since Glutathione is part of the body system that supports reduction of inflammation pathways in a unique aspect to detoxify the blood.

As shown above, by way of one or more embodiments, the patch showed wherein flexibility in the gut systems may be able to be restored. For example, as one ages there is often less flexibility in all the body systems. By way of at least one embodiment, the patch triggers change in the gut.

As shown above, by way of one or more embodiments, the patch showed wherein changes were in most of the types of amino acids and not limited to a single type of amino acid. For example, the changes included essential, non-essential, branched chain essential, aromatic and non-proteinogenic amino acids instead of a single amino acid or area of amino acid production.

As shown above, by way of one or more embodiments, the patch showed significant improvement (0.08) in short term memory within a week.

As shown above, for example, by way of at least one embodiment, the patch provides improvement in blood pressure, significant metabolic improvement, 17 statistically significant amino acid changes over the 7 days, significant improvement in anti-inflammatory response, improvement in sleep levels, reduction in blood pressure, improvement in memory, such as in short term memory, and improvement in reported feelings of vitality.

EXAMPLES

With respect to the non-transdermal patch, the following formulas may be utilized to create embodiments of the invention.

Example 1

TABLE 12

| At least one embodiment of the invention includes: | |
| --- | --- |
| Material | Amount |
| Distilled Water | 0.4 gallons |
| Vegetable Glycerin | 4.5 pounds |
| L-Lysine | 4 grams |
| GHK-Cu | 140 mg |
| Zinc Gluconate | 1 gram |
| Colloidal Copper 20 ppm | 50 ml |

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Lysine is measured on a scale to 4 grams and then added; this is allowed to mix for 1 minute. GHK-Cu is then added to the container in the amount of 140 mg, and this is allowed to mix for 1 minute. Zinc Gluconate is measured to the amount of 1 gram, and this is allowed to mix for 1 minute. Colloidal Copper is then added in the amount of 50 ml and mixed for 1 minute. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or one or more other embodiments of the invention.

Example 2

TABLE 13

| At least one embodiment of the invention includes: | |
| --- | --- |
| Material | Amount |
| Distilled Water | 0.4 gallons |
| Vegetable Glycerin | 4.5 pounds |
| L-Glutamine | 4 grams |
| GHK-Cu | 140 mg |
| Zinc Gluconate | 1 gram |
| Colloidal Copper 20 ppm | 50 ml |

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Glutamine is measured on a scale to 4 grams and then added; this is allowed to mix for 1 minute. GHK-Cu is then added to the container in the amount of 140 mg, and this is allowed to mix for 1 minute. Zinc Gluconate is measured to the amount of 1 gram, and this is allowed to mix for 1 minute. Colloidal Copper is then added in the amount of 50 ml and mixed for 1 minute. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 3

TABLE 14

| At least one embodiment of the invention includes: | |
| --- | --- |
| Material | Amount |
| Distilled Water | 0.4 gallons |
| Vegetable Glycerin | 4.5 pounds |
| L-Arginine | 4 grams |

TABLE 14-continued

At least one embodiment of the invention includes:

| Material | Amount |
| --- | --- |
| GHK-Cu | 140 mg |
| Zinc Gluconate | 1 gram |
| Colloidal Copper 20 ppm | 50 ml |

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Arginine is measured on a scale to 4 grams and then added; this is allowed to mix for 1 minute. GHK-Cu is then added to the container in the amount of 140 mg, and this is allowed to mix for 1 minute. Zinc Gluconate is measured to the amount of 1 gram, and this is allowed to mix for 1 minute. Colloidal Copper is then added in the amount of 50 ml and mixed for 1 minute. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 4

TABLE 15

At least one embodiment of the invention includes:

| Material | Amount |
| --- | --- |
| Distilled Water | 0.4 gallons |
| Vegetable Glycerin | 4.5 pounds |
| L-Glysine | 4 grams |
| GHK-Cu | 140 mg |
| Zinc Gluconate | 1 gram |
| Colloidal Copper 20 ppm | 50 ml |

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Glycine is measured on a scale to 4 grams and then added; this is allowed to mix for 1 minute. GHK-Cu is then added to the container in the amount of 140 mg, and this is allowed to mix for 1 minute. Zinc Gluconate is measured to the amount of 1 gram, and this is allowed to mix for 1 minute. Colloidal Copper is then added in the amount of 50 ml and mixed for 1 minute. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 5

TABLE 16

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| GHK-Cu | 140 mg |
| Zinc Gluconate | 1 gram |
| Colloidal Copper 20 ppm | 50 ml |

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. GHK-Cu is then added to the container in the amount of 140 mg, and this is allowed to mix for 1 minute. Zinc Gluconate is measured to the amount of 1 gram, and this is allowed to mix for 1 minute. Colloidal Copper is then added in the amount of 50 ml and mixed for 1 minute. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 6

TABLE 17

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| L-Lysine | 400 mg |
| Zinc Gluconate | 1 gram |
| Colloidal Copper 20 ppm | 50 ml |

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. L-Lysine is measured to an amount of 400 mg and then added and mixed for 1 minute. GHK-Cu is then added to the container in the amount of 150 mg, and this is allowed to mix for 1 minute. Zinc Gluconate is measured to the amount of 1 gram, and this is allowed to mix for 1 minute. Colloidal Copper is then added in the amount of 50 ml and mixed for 1 minute. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 7

TABLE 18

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| L-Lysine | 400 mg |
| GHK-Cu | 150 mg |
| Zinc Gluconate | 1 gram |

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. L-Lysine is measured to an amount of 400 mg and then added and mixed for 1 minute. GHK-Cu is then added to the container in the amount of 150 mg, and this is allowed to mix for 1 minute. Zinc Gluconate is measured to the amount of 1 gram, and this is allowed to mix for 1 minute. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 8

TABLE 19

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| L-Lysine | 400 mg |
| GHK-Cu | 150 mg |
| Zinc Gluconate | 1 gram |
| Malic Acid, Citric Acid | As needed to adjust pH |
| Potassium Sorbate | 1 gram |

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. L-Lysine is measured to an amount of 400 mg and then added and mixed for 1 minute. GHK-Cu is then added to the container in the amount of 150 mg, and this is allowed to mix for 1 minute. Zinc Gluconate is measured to the amount of 1 gram, and this is allowed to mix for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 9

TABLE 20

At least one embodiment of the invention includes:

| Material | Amount |
| --- | --- |
| Distilled Water | 0.4 gallons |
| Sodium Metasilicate | 500 mg |
| Vegetable Glycerin | 4.5 pounds |
| L-Carnitine | 4 grams |
| L-Lysine | 400 mg |
| GHK-Cu | 150 mg |
| Zinc Gluconate | 1 gram |
| Malic Acid, Citric Acid | As needed to adjust pH |
| Potassium Sorbate | 1 gram |

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. Sodium Metasilicate is measured to 500 mg and added to the container and then mixed for 1 minute. L-Lysine is measured to an amount of 400 mg and then added and mixed for 1 minute. GHK-Cu is then added to the container in the amount of 150 mg, and this is allowed to mix for 1 minute. Zinc Gluconate is measured to the amount of 1 gram, and this is allowed to mix for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 10

TABLE 21

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| L-Lysine | 400 mg |
| GHK-Cu | 150 mg |
| Zinc Gluconate | 1 gram |
| Malic Acid, Citric Acid | As needed to adjust pH |
| Potassium Sorbate | 1 gram |

According to at least one embodiment of the invention, a full spectrum light is setup so as to be positioned so that the output from the light goes thru a diffraction grating, and the now separated light comes into contact with a vessel containing 1 gallon of distilled water. The water is treated for a period of 24 hours prior to being used below.

A clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. L-Lysine is measured to an amount of 400 mg and then added and mixed for 1 minute. GHK-Cu is then added to the container in the amount of 150 mg, and this is allowed to mix for 1 minute. Zinc Gluconate is measured to the amount of 1 gram, and this is allowed to mix for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 11

TABLE 22

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| L-Lysine | 400 mg |
| GHK-Cu | 150 mg |
| Zinc Gluconate | 1 gram |
| Malic Acid, Citric Acid | As needed to adjust pH |
| Potassium Sorbate | 1 gram |

A double helix conductor as described in U.S. Pat. No. 8,653,925, entitled "Double Helix Conductor", to Schmidt, is setup on a fixture and is of such size that a glass vessel containing 1 gallon of water fits inside the center opening of the double helix conductor. The water is then treated for a period of 24 hours in accordance with the teachings of this invention prior to being used in the process below.

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. L-Lysine is measured to an amount of 400 mg and then added and mixed for 1 minute. GHK-Cu is then added to the container in the amount of 150 mg, and this is allowed to mix for 1 minute. Zinc Gluconate is measured to the amount of 1 gram, and this is allowed to mix for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 12

TABLE 23

At least one embodiment of the invention includes:

| Material | Amount |
| --- | --- |
| Distilled Water | 0.4 gallons |
| Vegetable Glycerin | 4.5 pounds |
| L-Glycine | 4 grams |
| L-Lysine | 400 mg |
| GHK-Cu | 150 mg |
| Zinc Gluconate | 1 gram |
| Malic Acid, Citric Acid | As needed to adjust pH |
| Potassium Sorbate | 1 gram |

A double helix conductor as described in U.S. Pat. No. 8,653,925, entitled "Double Helix Conductor", to Schmidt, is setup on a fixture and is of such size that a glass vessel containing 1 gallon of water fits inside the center opening of the double helix conductor. The water is then treated for a period of 24 hours in accordance with the teachings of this invention prior to being used in the process below.

According to at least one embodiment of the invention, a clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Glycine is measured on a scale to 4 grams and then added; this is allowed to mix for 1 minute. L-Lysine is measured to an amount of 400 mg and then added and mixed for 1 minute. GHK-Cu is then added to the container in the amount of 150 mg, and this is allowed to mix for 1 minute. Zinc Gluconate is measured to the amount of 1 gram, and this is allowed to mix for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 13

TABLE 24

At least one embodiment of the invention includes:

| Material | Amount |
| --- | --- |
| Distilled Water | 0.4 gallons |
| Vegetable Glycerin | 4.5 pounds |
| L-Glycine | 4 grams |
| L-Lysine | 400 mg |
| GHK-Cu | 150 mg |
| Zinc Gluconate | 1 gram |
| Malic Acid, Citric Acid | As needed to adjust pH |
| Potassium Sorbate | 1 gram |

A double helix conductor as described in U.S. Pat. No. 8,653,925, entitled "Double Helix Conductor", to Schmidt, is setup on a fixture and is of such size that a glass vessel containing 1 gallon of water fits inside the center opening of the double helix conductor. The water is then treated for a period of 24 hours in accordance with the teachings of this invention prior to being used in the process below.

According to at least one embodiment of the invention, the container below is setup using a lily impeller or other mixing blade such that the water-based solution below will vortex as it is mixed.

A clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Glycine is measured on a scale to 4 grams and then added; this is allowed to mix for 1 minute. L-Lysine is measured to an amount of 400 mg and then added and mixed for 1 minute. GHK-Cu is then added to the container in the amount of 150 mg, and this is allowed to mix for 1 minute. Zinc Gluconate is measured to the amount of 1 gram, and this is allowed to mix for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 14

TABLE 25

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| L-Lysine | 400 mg |
| GHK-Cu | 150 mg |
| Zinc Gluconate | 1 gram |
| Malic Acid, Citric Acid | As needed to adjust pH |
| Potassium Sorbate | 1 gram |

A double helix conductor as described in U.S. Pat. No. 8,653,925, entitled "Double Helix Conductor", to Schmidt, is setup on a fixture and is of such size that a glass vessel containing 1 gallon of water fits inside the center opening of the double helix conductor. The water is then treated for a period of 24 hours in accordance with the teachings of this invention prior to being used in the process below.

According to at least one embodiment of the invention, the container below is setup using a lily impeller or other mixing blade such that the water-based solution below will vortex as it is mixed.

A clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. L-Lysine is measured to an amount of 400 mg and then added and mixed for 1 minute. GHK-Cu is then added to the container in the amount of 150 mg, and this is allowed to mix for 1 minute. Zinc Gluconate is measured to the amount of 1 gram, and this is allowed to mix for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 15

TABLE 26

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| GHK-Cu | 150 mg |
| Zinc Gluconate | 1 gram |
| Malic Acid, Citric Acid | As needed to adjust pH |
| Potassium Sorbate | 1 gram |

A double helix conductor as described in U.S. Pat. No. 8,653,925, entitled "Double Helix Conductor", to Schmidt, is setup on a fixture and is of such size that a glass vessel containing 1 gallon of water fits inside the center opening of the double helix conductor. The water is then treated for a period of 24 hours in accordance with the teachings of this invention prior to being used in the process below.

According to at least one embodiment of the invention, the container below is setup using a lily impeller or other mixing blade such that the water-based solution below will vortex as it is mixed.

A clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. GHK-Cu is then added to the container in the amount of 150 mg, and this is allowed to mix for 1 minute. Zinc Gluconate is measured to the amount of 1 gram, and this is allowed to mix for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 16

TABLE 27

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| GHK | 150 mg |
| Zinc Gluconate | 1 gram |
| Colloidal Copper 20 ppm | 50 ml |
| Malic Acid, Citric Acid | As needed to adjust pH |
| Potassium Sorbate | 1 gram |

A double helix conductor as described in U.S. Pat. No. 8,653,925, entitled "Double Helix Conductor", to Schmidt, is setup on a fixture and is of such size that a glass vessel containing 1 gallon of water fits inside the center opening of the double helix conductor. The water is then treated for a period of 24 hours in accordance with the teachings of this invention prior to being used in the process below.

According to at least one embodiment of the invention, the container below is setup using a lily impeller or other mixing blade such that the water-based solution below will vortex as it is mixed.

A clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. GHK is then added to the container in the amount of 150 mg, and this is allowed to mix for 1 minute. Zinc Gluconate is measured to the amount of 1 gram, and this is allowed to mix for 1 minute. Colloidal Copper is measured to 50 ml and then added to the container and mixed for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 17

TABLE 28

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| AHK-Cu | 150 mg |
| Zinc Gluconate | 1 gram |
| Colloidal Copper 20 ppm | 50 ml |
| Malic Acid, Citric Acid | As needed to adjust pH |
| Potassium Sorbate | 1 gram |

A double helix conductor as described in U.S. Pat. No. 8,653,925, entitled "Double Helix Conductor", to Schmidt, is setup on a fixture and is of such size that a glass vessel containing 1 gallon of water fits inside the center opening of the double helix conductor. The water is then treated for a period of 24 hours in accordance with the teachings of this invention prior to being used in the process below.

According to at least one embodiment of the invention, the container below is setup using a lily impeller or other mixing blade such that the water-based solution below will vortex as it is mixed.

A clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. AHK-Cu is then added to the container in the amount of 150 mg, and this is allowed to mix for 1 minute. Zinc Gluconate is measured to the amount of 1 gram, and this is allowed to mix for 1 minute. Colloidal Copper is measured to 50 ml and then added to the container and mixed for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 18

TABLE 29

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| AHK | 150 mg |
| Zinc Gluconate | 1 gram |
| Colloidal Copper 20 ppm | 50 ml |
| Malic Acid, Citric Acid | As needed to adjust pH |
| Potassium Sorbate | 1 gram |

A double helix conductor as described in U.S. Pat. No. 8,653,925, entitled "Double Helix Conductor", to Schmidt, is setup on a fixture and is of such size that a glass vessel containing 1 gallon of water fits inside the center opening of the double helix conductor. The water is then treated for a period of 24 hours in accordance with the teachings of this invention prior to being used in the process below.

According to at least one embodiment of the invention, the container below is setup using a lily impeller or other mixing blade such that the water-based solution below will vortex as it is mixed.

A clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. AHK is then added to the container in the amount of 150 mg, and this is allowed to mix for 1 minute. Zinc Gluconate is measured to the amount of 1 gram, and this is allowed to mix for 1 minute. Colloidal Copper is measured to 50 ml and then added to the container and mixed for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Example 19

TABLE 30

At least one embodiment of the invention includes:

| Material | Amount |
| --- | --- |
| Distilled Water | 0.4 gallons |
| Vegetable Glycerin | 4.5 pounds |
| L-Carnitine | 4 grams |
| L-Alanine | 400 mg |
| AHK-Cu | 150 mg |
| Zinc Gluconate | 1 gram |
| Colloidal Copper 20 ppm | 50 ml |
| Malic Acid, Citric Acid | As needed to adjust pH |
| Potassium Sorbate | 1 gram |

A double helix conductor as described in U.S. Pat. No. 8,653,925, entitled "Double Helix Conductor", to Schmidt, is setup on a fixture and is of such size that a glass vessel containing 1 gallon of water fits inside the center opening of the double helix conductor. The water is then treated for a period of 24 hours in accordance with the teachings of this invention prior to being used in the process below.

According to at least one embodiment of the invention, the container below is setup using a lily impeller or other mixing blade such that the water-based solution below will vortex as it is mixed.

A clean and dry container is placed on a scale, having a capacity of at least 1 gallon. Glycerin is dispensed into the container and measured to be 4.5 pounds. Distilled water is then added to the container in the amount of 0.4 Gallons. The contents are then mixed for 1 minute until by visual inspection a uniform mixture has been obtained. Optionally, a magnetic mixer may be used, and the mixer is left on for the full duration of the processing. After the glycerin and water have mixed together, the L-Carnitine is measured on a scale to 4 grams and then added; this is allowed to mix for 1 minute. L-Alanine is measured to 400 mg and then added and mixed for 1 minute. AHK-Cu is then added to the container in the amount of 150 mg, and this is allowed to mix for 1 minute. Zinc Gluconate is measured to the amount of 1 gram, and this is allowed to mix for 1 minute. Colloidal Copper is measured to 50 ml and then added to the container and mixed for 1 minute. At this point Malic Acid and Citric Acid may be introduced to pH adjust and balance the solution as needed. 1 gram of Potassium Sorbate is then added and allowed to mix for 5 minutes. The solution is then mixed for an additional 10 minutes or until a uniform solution has been formed, with no solids in the solution. This will make about 1 gallon of solution. This container is then sealed and then transferred to a cold storage unit, operating at a temperature above freezing, for a period of at least 24 hours. The solution may then be dispensed and placed into patches or other embodiments of the invention.

Anti-Viral Embodiments

Embodiments may include, or be used with, copper glycinate as an anti-viral therapy or an anti-inflammatory or both. At least one embodiment may be utilized to treat the novel coronavirus (COVID-19) through light mediated synthesis of copper peptide and mobilization of copper ions for example. Benefits of this therapy include:
  Produces rapid alterations in blood chemistry for powerful antiviral effects
  Large body of evidence to support efficacy
  Simple to administer
  Reduced risk of toxic side effects
  Inexpensive
  Large scale manufacturing already in place for immediate deployment Embodiments of the invention target viruses through use of embodiments of the patch 100 described herein and as shown in FIG. 1, along with administration of any form of bioavailable copper, for example copper glycinate 101, (or copper gluconate, copper sulfate, copper carbonate, colloidal copper, or any other form of bioavailable copper) in one embodiment administered orally, in other embodiments via transdermal patches (e.g., in embodiments with a combined transdermal patch if so equipped at 100 or via separate transdermal patch 102a), or via injection, combined with embodiments described herein for example that are configured to light mediate the synthesis of peptide GHK that binds to copper for producing powerful antiviral effects. Embodiments may also include an anti-inflammatory, either taken orally 102b, or via transdermal patch 102a, wherein the anti-inflammatory may include any COX-2 inhibitor or any steroidal anti-inflammatory or any other type of anti-inflammatory compound.

While copper has demonstrated the ability to inactivate viruses on surfaces (Warnes et al., 2015), copper is also a naturally occurring component of skin and connective tissue. In the human body, copper ions bind to specific peptides that have important metabolic functions in human beings.

Copper ions appear to attack viruses in two different ways, using two different types of ions. The first, Cu(II), attacks the capsid barrier (Manuel et al., 2015), and this starts with the virus's receptor sites, immediately limiting its ability to infect individuals even before virus death (Manuel et al., 2015). Damaging viral receptor sites have been shown to decrease infectiousness within 2 min. in a Norovirus strand (Manuel et al., 2015).

The second ion Cu(I) goes after the genome (Warnes et al., 2015). It appears that one of the nucleic acids forms covalent bonds with copper, and in the process, divides the genome into pieces (Borkow et al., 2009). It appears that these nucleotides can occur as often as every three nucleotides (Borkow et al., 2009). This means that the genome divides into progressively smaller sections over time (Warnes et al., 2015). This has been seen to start within 15 minutes and leaves no viable virus by 2 hrs (Manuel et al., 2015). The DNA damage was found to still occur with nanoparticles of copper, and not just with solid objects (Fujimori et al., 2012). It also means that the genomic information will not be available for other viruses to integrate and mutate (Warnes et al., 2015).

Copper has a long history of use in medicine, starting with the purification of drinking water and burns (Borkow et al., 2009.) It has continued to be used for purification of water, including use in hospitals to prevent legionnaires disease (Borkow et al., 2009). It also has EPA approval for use as an antimicrobial surface (Borkow et al., 2009).

"Copper has previously been implicated in the regulation of immune responses . . . (Hu Frisk et al., 2017)." There are studies demonstrating its ability to kill a number of different viruses, including HIV and Polio (Borkow et al., 2009). The CDC has recently pre-released information on a study completed in March 2020 on the lifespan of COVID-19 on different surfaces (van Doremalen et al., 2020). This included the lifespan on copper, where it was completely dead within 4 hours (van Doremalen et al., 2020.)

A 2015 study found that the " . . . immune system responds to infections with *M. tuberculosis* by overloading the phagosome with copper and zinc . . . (Neyrolles et al., 2015)." It should also be noted that, aside from decreasing the microbial burden itself, copper also appears to have an antimicrobial effect on its surroundings, and one which has been tested and remained consistent for 21 months (Schmidt et al., 2012). "The levels of antimicrobial activity of the metallic copper surfaces were equivalent throughout the course of the trial (Schmidt et al., 2012)." "The most surprising finding was the 64% decrease in MB between the preintervention and intervention phases in the control rooms (Schmidt et al., 2012)."

In an article published in the New England Journal of Medicine on Mar. 17, 2020:
  Aerosol and Surface Stability of SARS-CoV-2 as Compared with SARS-CoV-1 http://www.nejm.org/doi/10.1056/NEJMc2004973
  On copper, no viable SARS-CoV-2 was measured after 4 hours, and no viable SARS-CoV-1 was measured after 8 hours.

In other research from the University of Southampton, evaluation of the ability of copper to immobilize viruses produced significant results:

Using copper to prevent the spread of respiratory viruses http://www.sciencedaily.com/release/2015/11/151110102147.htm New research from the University of Southampton has found that copper can effectively help to prevent the spread of respiratory viruses, which are linked to severe acute respiratory syndrome (SARS) and the Middle East respiratory syndrome (MERS).

While this research points to the use of antimicrobial copper for inactivating viruses on a surface, embodiments of the invention seek to produce the same effect within the human body. The following study indicates that this is possible:

Mechanism of Copper-Mediated Inactivation of Herpes Simplex Virus http://www.aac.asm.org/content/aac/41/4/812.full.pdf This study concluded that "The sensitivity exhibited by HSV to Cu(II) and reducing agents, particularly ascorbate, might be useful in the development of therapeutic antiviral agents (Sagripanti et al., 1997)."

Embodiments of the invention may utilize a suitable efficacious amount of supplemental copper (such as 2 mg copper glycinate, twice daily) along with embodiments of the invention that produce light-mediated increase of GHK-Cu, a natural copper peptide.

GHK is a simple peptide that has a very high affinity for copper. GHK-Cu naturally occurs in the human body but declines with age (Pickart & Margolina, 2018). GHK-Cu has a number of significant beneficial effects on human beings such as:

improved energy metabolism and immune function
improves wound healing and tissue regeneration
possesses DNA repair, antioxidant, and anti-inflammatory effects
regulation of GABA for improved sleep
increases cellular stemness, secretion of trophic factors by mesenchymal stem cells
increased expression of P63 for increased proliferation of stem cells However, perhaps the most profound attribute of GHK-Cu is its ability to modulate gene expression, resetting thousands of genes to a more youthful state (Pickart et al., 2015; Pickart & Margolina, 2018).

Regenerative and Protective Actions of the GHK-Cu Peptide in the Light of the New Gene Data http://www.ncbi.nlm.nih.gov/pmc/articles/PMC6073405/

As a result of this attribute of GHK-Cu, it has been discovered in prior research that improvements in immune response, reduction in inflammatory markers, facilitation in the repair of lung tissue from acute lung injury, and general wound healing all improve. "The use of GHK-Cu in mice protected their lung tissue from induced acute lung injury (ALI) and suppressed the infiltration of inflammatory cells into the lung. The GHK-Cu also increased superoxide dismutase (SOD) activity while decreasing TNF-1 and IL-6 production through the blocking activation of NFκB's p65 and p38 MAPK (mitogen activated protein kinase) (Pickart & Margolina, 2018)." Improving these factors would be of tremendous value in the event of a viral infection that causes lung inflammation, destruction, and organ failure.

To rapidly elevate GHK-Cu, at least one embodiment of the invention, namely a wearable, nanotechnology device that is applied to the patient's skin is utilized. Embodiments of the invention, powered by body heat, reflect specific wavelengths of light to the surface of the skin, stimulating the production of GHK-Cu, instead of providing copper peptide by injection or oral supplementation. The effect is known as photobiomodulation. Embodiments have been tested and show that GHK is elevated to significance within the first 24 hours of application to the skin. The blood samples were processed according to the original thesis of Dr. Pickard. There was a significant increase in GHK in the blood, which was seen at 24 hours, at the level of $p<0.0098$. A significant increase in GHK-Cu in the blood was also seen at 7 days at the level of $p<0.0137$.

Testing Results

Testing results that demonstrates how embodiments of the patch consistently reflect wavelengths of light follows.

Equipment utilized included a Patch assembly machine, specifically a Shimadzu FTIR IR Affinity Series.

Embodiments of the phototherapy patches include a polyester patch contained between two layers of clear polyethylene film. The polymer shell is constructed from water-resistant medical grade polyethylene. The top side of the patch is composed of water-resistant polyethylene film that is sealed to the bottom portion of the patch that is composed of water-resistant single coated medical grade polyethylene tape. The polyethylene tape is coated with a hypoallergenic pressure sensitive acrylate adhesive that is utilized to adhere the patch to the body. The polyester patch is treated with water-based solutions containing for example distilled water, glycerol and material listed previously herein. No ingredients enter the body. All product was inspected for conformance to release criteria prior to testing with no issue.

Fourier-transform infrared spectroscopy (FTIR) was the technique used to obtain an infrared spectrum of absorption or emission of a solid, liquid or gas with respect to an embodiment of the invention. An FTIR spectrometer simultaneously collects high-spectral-resolution data over a wide spectral range.

Once the seal of the patch stays intact the infrared spectrum of absorption of the patch should remain the same over time. This test compared the spectra produced by the patches at 3-time frames, T0 0 months, T1 18 months and T2, 24 months. Specifically, the product was prepared for testing by cutting the patch carefully around the non-woven shape, allowing the saturated non-woven to be separated from the laminate and the backing. Gloves were used to ensure minimal contamination of the sample. Samples were tested as per in house validated procedures. A median sample was determined at the T0 time point was then used as a comparison for purity calculations. The median was determined by inspecting multiple samples at once determining a median and repeating. The medians of each group were then compared to determine the medians of the medians and this was used as the overall 'standard' for the patch. The T0 spectra was compared against T1 and T—see below for sample size and acceptance criteria

| Time Point | Product Specification | Acceptance Criteria | Sample Size Rational |
|---|---|---|---|
| T0, T1, T2 | All samples must be tested as per in house procedure | The spectra generated for T0 standard must visually be equivalent to other T0 samples. T1, T2 - The purity calculation between T0 standard and | As per in house process risk management procedures, a Risk Priority Number of 10 is associated with this product. As per in house procedures, RPN of 10 equates to a sample of 29 patches |

| Time Point | Product Specification | Acceptance Criteria | Sample Size Rational |
|---|---|---|---|
| | | T0 must be > 0.9 | which were tested. |
| | | T1 must be > 0.9 | T0 – 29 samples |
| | | T2 must be > 0.9 | T1 – 29 samples |
| | | | T2 – 29 samples |

Results are shown in FIG. 12, i.e., a Visual Comparison of a sample of patch spectra at T0 (Black), T1 (Blue), and T2 (Red).

FTIR Purity for the patches at T1 and T2 were tested after prepared for testing by cutting the patch around the nonwoven shape as described above wherein purity calculations were conducted comparing the T1 and T2 samples to the T0 sample obtained. The T0 standard used was sample number 1.

| T0 v T0 | |
|---|---|
| Sample Number | Purity Index |
| 1 | Standard |
| 2 | 0.9899 |
| 3 | 0.9099 |
| 4 | 0.9638 |
| 5 | 0.9820 |
| 6 | 0.9790 |
| 7 | 0.9919 |
| 8 | 0.9772 |
| 9 | 0.9795 |
| 10 | 0.9733 |
| 11 | 0.9691 |
| 12 | 0.9951 |
| 13 | 0.9935 |
| 14 | 0.9444 |
| 15 | 0.9958 |
| 16 | 0.9843 |
| 17 | 0.9593 |
| 18 | 0.9857 |
| 19 | 0.9894 |
| 20 | 0.9833 |
| 21 | 0.9871 |
| 22 | 0.9730 |
| 23 | 0.9661 |
| 24 | 0.9785 |
| 25 | 0.9688 |
| 26 | 0.9278 |
| 27 | 0.9588 |
| 28 | 0.9527 |
| 29 | 0.9430 |

The results obtained indicated that the samples at T0 were very similar (all >0.9278 similarity) to the standard of the contents of the patch at T0, sample 1. The average purity index of the 29 samples was 0.971507. These results meet the acceptance criteria of >0.9.

| T0 v T1 | |
|---|---|
| Sample Number | Purity Index |
| 1 | 0.9803 |
| 2 | 0.9711 |
| 3 | 0.9710 |
| 4 | 0.9794 |
| 5 | 0.9840 |
| 6 | 0.9861 |
| 7 | 0.9804 |
| 8 | 0.9673 |
| 9 | 0.9880 |
| 10 | 0.9819 |
| 11 | 0.9909 |
| 12 | 0.9704 |
| 13 | 0.9939 |
| 14 | 0.9743 |
| 15 | 0.9720 |
| 16 | 0.9825 |
| 17 | 0.9804 |
| 18 | 0.9837 |
| 19 | 0.9694 |
| 20 | 0.9748 |
| 21 | 0.9660 |
| 22 | 0.9965 |
| 23 | 0.9759 |
| 24 | 0.9748 |
| 25 | 0.9969 |
| 26 | 0.9931 |
| 27 | 0.9786 |
| 28 | 0.9929 |
| 29 | 0.9908 |

The results obtained indicated that the samples at T1 were very similar (all >0.9673 similarity) to the standard of the contents of the patch at T0. The average purity index of the 29 samples was 0.980589. These results meet the acceptance criteria of >0.9.

| T0 v T2 | |
|---|---|
| Sample Number | Purity Index |
| 1 | 0.9714 |
| 2 | 0.9793 |
| 3 | 0.9870 |
| 4 | 0.9842 |
| 5 | 0.9780 |
| 6 | 0.9807 |
| 7 | 0.9904 |
| 8 | 0.9818 |
| 9 | 0.9813 |
| 10 | 0.9881 |
| 11 | 0.9781 |
| 12 | 0.9797 |
| 13 | 0.9905 |
| 14 | 0.9778 |
| 15 | 0.9849 |
| 16 | 0.9784 |
| 17 | 0.9835 |
| 18 | 0.9940 |
| 19 | 0.9884 |
| 20 | 0.9821 |
| 21 | 0.9827 |
| 22 | 0.9767 |
| 23 | 0.9784 |
| 24 | 0.9722 |
| 25 | 0.9762 |
| 26 | 0.9862 |
| 27 | 0.9826 |
| 28 | 0.9722 |
| 29 | 0.9810 |

The results obtained indicated that the samples at T2 were very similar (all >0.9714 similarity) to the standard of the contents of the patch at T0. The average purity index of the 29 samples was 0.981671. These results meet the acceptance criteria of >0.9.

Testing conclusion. Data generated through FTIR analysis shows that the spectrum of patches between 4600-600 nm is consistent in reflecting light and is also comparable to itself not only when product is newly manufactured but for the duration of its shelf life. The spectrum is consistent not only upon visual inspection, but purity calculations conducted also determined very high levels of similarity in the samples.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A wearable phototherapy system configured to be applied to a subject's body to provide a beneficial effect for the subject selected from a group consisting of activation of stem cells, an improvement in energy, an elevation of antioxidants, a reduction in inflammation, an elevation of collagen production, an improvement in wound healing, an increase in strength, an increase in stamina, a relief from pain and an improvement in strength endurance, the wearable phototherapy system comprising:
a non-transdermal container configured to provide a beneficial biological effect, wherein
said non-transdermal container comprises
matter that comprises at least one Left-Handed molecule comprising at least one Left-Handed organic molecule or at least one Left-Handed inorganic molecule or both said at least one Left-Handed organic molecule and said at least one Left-Handed inorganic molecule,
wherein said at least one Left-Handed molecule further comprises a material pre-selected configured to interact with infrared light; and,
at least one phototherapy layer comprising
glycyl-L-histidyl-Lysine (GHK) or copper binding peptide glycyl-L-histidyl-Lysine (GHK-Cu) or alanyl-L-histidyl-L-Lysine (AHK) or copper binding peptide alanyl-L-histidyl-L-Lysine (AHK-Cu), or any combination thereof;
wherein, via said at least one phototherapy layer, the matter in the non-transdermal container is configured to reflect or emit specific wavelengths of light into said subject's body after said matter is stimulated by said infrared light wherein said specific wavelengths of light elevate levels of copper binding peptide glycyl-L-histidyl-Lysine (GHK-Cu) in said subject's body;
wherein the non-transdermal container is configured to prevent the at least one Left-Handed molecule from direct contact with the subject's body.

2. The wearable phototherapy system of claim 1, wherein said non-transdermal container further comprises one or more of:
at least one amino acid,
at least one amino acid derivative,
sodium metasilicate,
zinc gluconate, or
colloidal copper.

3. The wearable phototherapy system of claim 1, wherein to provide the beneficial effect of increase in strength or an improvement in strength endurance, the at least one Left-Handed molecule is an amino acid, wherein the amino acid is selected from the group consisting of L-Arginine, L-Carnitine, Acetyl-L-Carnitine, L-Glutamine, L-Methionine, L-Ornithine, and L-Taurine.

4. The wearable phototherapy system of claim 1, wherein to provide the beneficial effect of increase in strength or an improvement in strength endurance, the at least one Left-Handed molecule is an amino acid selected from L-Carnitine and Acetyl-L-Carnitine.

5. The wearable phototherapy system of claim 1, wherein the non-transdermal container further comprises an enclosure, wherein the enclosure is made of a plastic film selected from the group consisting of polyethylene, polypropylene, Acrylonitrile Butadiene Styrene (ABS), plexiglass, polycarbonate, light polarizing film, and linear low-density film.

6. The wearable phototherapy system of claim 1, wherein the non-transdermal container further comprises an enclosure, wherein the enclosure further comprises or couples with one or more adhesive portions to permit attachment the subject's body.

7. The wearable phototherapy system of claim 1, wherein said non-transdermal container further comprises one or more additives that are selected from a group consisting of glycerin, d-calcium pantothenate, sorbitol, propylparaben, potassium sorbate, methylparaben, and colloidal gold.

8. The wearable phototherapy system of claim 1, wherein said non-transdermal container is a patch constructed in layers, the layers comprising one or more of:
a plastic film as an enclosure,
a light polarizing film as an enclosure,
a polyester fabric as a substrate,
water,
L-Carnitine,
glycerin,
d-calcium pantothenate,
sorbitol,
propylparaben,
potassium sorbate, or
methylparaben.

9. The wearable phototherapy system of claim 1, wherein said at least one phototherapy layer comprises a first phototherapy layer and a second phototherapy layer.

10. The wearable phototherapy system of claim 9, wherein said first phototherapy layer and said second phototherapy layer are one or more of:
layered on top of each other,
coupled directly or indirectly, or
layered as concentric rings.

11. The wearable phototherapy system of claim 9, wherein via said first phototherapy layer and said second phototherapy layer, the non-transdermal container reflects different wavelengths of light from each layer of said first phototherapy layer and said second phototherapy layer.

12. The wearable phototherapy system of claim 1, wherein the non-transdermal container further comprises at least one ball or bead.

13. The wearable phototherapy system of claim 1, further comprising a transdermal container, wherein the transdermal container is coupled to said non-transdermal container.

14. The wearable phototherapy system of claim 1, further configured to provide an anti-viral effect via said wearable phototherapy system in combination with bioavailable copper, copper gluconate, copper sulfate, copper carbonate, colloidal copper, copper glycinate, or any combination thereof that is configured to be applied to said subject's body via a pill or via an injection.

15. The wearable phototherapy system of claim 1, further comprising an anti-inflammatory agent configured to be applied to said subject's body via a pill and configured to be utilized with said wearable phototherapy system or via a transdermal container coupled to said non-transdermal container within said wearable phototherapy system.

16. The wearable phototherapy system of claim 1, further comprising:
- a substrate in the non-transdermal container which contains the at least one Left-Handed molecule, and
- an enclosure that encloses the substrate and the at least one phototherapy layer, and
- wherein said non-transdermal container is configured to pass said infrared light and said specific wavelengths of light that elevate GHK-Cu in said subject's body.

17. The wearable phototherapy system of claim 13, wherein said transdermal container comprises at least one of bioavailable copper, copper gluconate, copper sulfate, copper carbonate, colloidal copper, and copper glycinate.

* * * * *